(12) United States Patent
Cauwenberghs et al.

(10) Patent No.: US 7,622,259 B1
(45) Date of Patent: Nov. 24, 2009

(54) DETECTION OF VON-WILLEBRAND FACTOR (VWF) ACTIVITY

(75) Inventors: Nancy Cauwenberghs, Londearzeel (BE); Karen Vanhoorelbeke, Zwevegem (BE); Hans Deckmyn, Linden (BE)

(73) Assignee: K.U. Leuven Research & Development, Leuven (BE)

( * ) Notice: Subject to any disclaimer, the term of this patent is extended or adjusted under 35 U.S.C. 154(b) by 315 days.

(21) Appl. No.: 10/019,740

(22) PCT Filed: Jul. 5, 2000

(86) PCT No.: PCT/EP00/06345

§ 371 (c)(1),
(2), (4) Date: May 8, 2002

(87) PCT Pub. No.: WO01/02853

PCT Pub. Date: Jan. 11, 2001

(30) Foreign Application Priority Data

Jul. 5, 1999 (EP) .................................. 99112967

(51) Int. Cl.
*G01N 33/53* (2006.01)
*G01N 33/60* (2006.01)
*G01N 33/536* (2006.01)
*G01N 33/541* (2006.01)
*G01N 33/543* (2006.01)
*G01N 33/552* (2006.01)
*G01N 33/566* (2006.01)
*G01N 33/577* (2006.01)
*G01N 21/75* (2006.01)
*G01N 21/76* (2006.01)
*G01N 21/78* (2006.01)

(52) U.S. Cl. .................. 435/7.1; 435/7.9; 435/7.91; 435/7.92; 435/69.1; 435/69.6; 435/70.3; 436/501; 436/504; 436/517; 436/518; 436/528; 436/164; 436/172; 436/805; 436/819

(58) Field of Classification Search ................ 435/7.1, 435/69.1, 69.6, 70.3; 436/501, 517, 518, 436/528, 805, 819
See application file for complete search history.

(56) References Cited

U.S. PATENT DOCUMENTS 4,415,700 A * 11/1983 Batz et al. .................. 524/548

(Continued)

FOREIGN PATENT DOCUMENTS

| WO | 92/16225 | 10/1992 |
|---|---|---|
| WO | 01/02853 | 1/2001 |

OTHER PUBLICATIONS

Murata, M. et al., "Site-directed mutagenesis of a soluble recombinant fragment of platelet glycoprotein Ibα demonstrating negatively charged residues involved in von Willebrand factor binding", 1991, J Biol Chem, vol. 266, pp. 15474-15480.*

(Continued)

*Primary Examiner*—Unsu Jung
(74) *Attorney, Agent, or Firm*—Burns & Levinson LLP; Ronda P. Moore

(57) ABSTRACT

The present invention relates to a method for detecting von-Willebrand factor (vWF) activity comprising assaying a sample in the presence of a soluble form or portion of glycoprotein Ib(α) (GPIb(α) and ristocetin, or a functionally equivalent substance. Additionally, the invention relates to the use of the aforementioned soluble form or portion of glycoprotein Ib(α), of ristocetin or a functional equivalent substance, of specifically reacting anti-GPIB(α) antibody(ies) and/or of specific binding partners, like specifically reacting anti-vWF antibody(ies) for carrying out the method of the invention. Furthermore, the present invention relates to kits for carrying out the method of the invention.

21 Claims, 9 Drawing Sheets

U.S. PATENT DOCUMENTS

Figure 1:
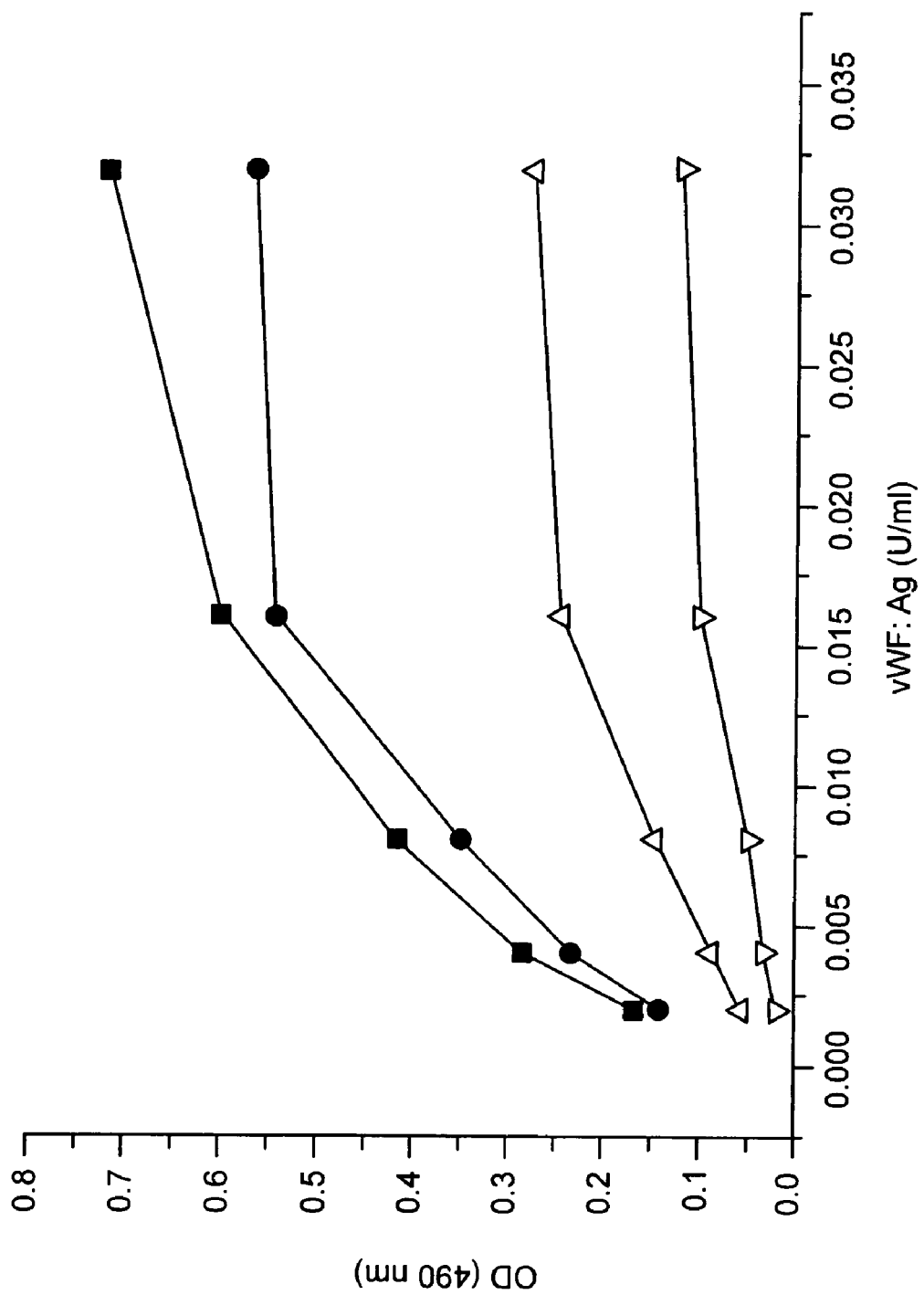

| | | | | |
|---|---|---|---|---|
| 4,537,861 | A | * | 8/1985 | Elings et al. ................ 436/518 |
| 5,231,033 | A | | 7/1993 | Fickenscher |
| 5,317,097 | A | * | 5/1994 | Miller et al. ............. 536/24.31 |
| 5,321,127 | A | * | 6/1994 | Handin ....................... 530/383 |
| 5,837,488 | A | * | 11/1998 | Garfinkel et al. ........... 435/69.1 |
| 6,043,871 | A | * | 3/2000 | Solen et al. ................... 356/39 |
| 6,228,613 | B1 | * | 5/2001 | Fischer et al. .............. 435/69.1 |

OTHER PUBLICATIONS

Favaloro et al., "Von-Willebrand's diseas: laboratory investigation using an improved functional assay for von Willebrand factor", Pathology, 1993, vol. 25, pp. 152-158.*

Hoylaerts et al., "Promotion of binding of von Willebrand factor ot platelet glycoprotein by dimers of ristocetin", Biochem. J., 1995, vol. 386, pp. 453-463.*

Christophe et al., "Influence of Mutations and Size of Multimers in Type II von Willebrand Disease Upon the Function of von Willebrand Factor", Blood, 1994, vol. 83, pp. 3553-3561.*

Favaloro, "Laboratory assessment as a critical component of the appropriate diagnosis and sub-classification of von Willebrand's disease", Blood Review, 1999, vol. 13, pp. 185-204.*

Michelson et al., "Partial characterization of a binding site for von Willebrand factor on glycocalicin", Blood, 1986, vol. 67, pp. 19-26.*

Vanhoorelbeke et al., "Plasma glycocalicin as a source of GP1b-alpha in the von Willebrand factor ristocetin cofactor ELISA", Thromb. Haemost., 2005, vol. 93, pp. 165-171.*

Murray et al., "von Willebrand disease: pathogenesis, classification, and management," Transfusion Medicine Reviews, 1996, vol. X, pp. 93-110.*

Tefferi et al., "Acquired von Willebrand disease: concise review of occurrence, diagnosis, pathogenesis, and treatment," Am. J. Med., 1997, vol. 103, pp. 536-540.*

Vischer et al, "von Willebrand factor: from cell biology to the clinical management of von Willebrand's disease," Critical Reviews in Oncology/Hematology, 1999, vol. 30, pp. 93-109.*

Zieger et al, "New families with von Willebrand disease type 2M (Vicenza)," Thrombosis Research, 1997, vol. 87, pp. 57-64.*

Aihara et al., (1988), "Plasma Collagen Cofactor Correlates with von Willebrand Factor Antigen and Ristocetin Cofactor but Not with Bleeding Time," *Thromb. Haemost.*, 59(3):485-490.

Berliner et al., (1988), Generation and Characterization of Peptide-specific Antibodies That Inhibit Von Willebrand Factor Binding to Glycoprotein IIb-IIIa without Interacting with Other Adhesive Molecules, *J. Bio. Chem.*, 263:7500-7505.

Brown et al., (1986), "An ELISA Test for the Binding of von Willebrand Antigen to Collagen," *Thromb Res.*, 43:303-311.

Casonato et al., (1998), "The Evaluation of Factor VIII Binding Activity of von Willebrand Factor by Means of an ELISA Method, Significance and Practical Implications," *Am. J. Clin. Path.*, 109:347-352.

De Marco et al., (1986), "von Willebrand Factor Interaction with the Glycoprotein IIb/IIIa Complex, Its role in Platelet Function as Demonstrated in Patients with Congenital Afibrinogenemia," *J. Clin. Invest.*, 77:1272-1277.

Depraetere et al., (1988), "Platelet Aggregation Induced by a Monoclonal Antibody of the A1 Domain of von Willebrand Factor," *Blood*, 91:3792-3799.

Ewenstein, (1997), "Von Willebrand's Disease," *Annu. Rev. Med.*, 48:525-542.

Falkenberg et al., (1995), "In vitro production monoclonal antibodies in high concentration in a new and easy to handle modular minifermenter," *J. Immunol, Methods*, 179:13-29.

Favalore et al., (1991), "Development of a simple collagen based ELISA assay aids in the diagnosis of, and permits sensitive discrimination between Type I and Type II, von Willebrand's disease," *Blood Coagul. Fibrinolysis*, 2:285-291.

Favaloro et al., (1993), "von Willebrand's Disease: Laboratory Investigation Using an Improved Functional Assay for von Willebrand Factor," *Pathology*, 25:152-158.

Favaloro et al., (1995), "Laboratory Assessment of von Willebrand Factor, Use of Different Assays Can Influence the Diagnosis of von Willebrand's Disease, Dependent on Differing Sensitivity to Sample Preparation and Differential Recognition of High Molecular Weight VWF Forms," *Am. J. Clin. Pathol.*, 104:(3)264-271.

Favaloro et al, (1997), "Laboratory Assays For von Willebrand Factor: Relative Contribution to the Diagnosis of von Willebrand's Disease," *Pathology*, 29:385-91.

Federici et al., (1989), "Binding of von Willebrand factor to glycoproteins Ib and IIb/IIIa complex: affinity is related to multimeric size," *Br. J. Haemato.*, 73:93-99.

Federici et al., (2004), "A sensitive ristocetin co-factor activity assay with recombinant glycoprotein Ibα for the diagnosis of patients with low von Willebrand factor levels," *Haematologica*, 89:77-85.

Fischer et al., (1996), "Effect of Multimerization of Human and Recombinant von Willebrand Factor on Platelet Aggregation, Binding to Collagen and Binding of Coagulation Factor VIII," *Thromb. Res.*, 84(1):55-66.

Fischer et al., (1998), "von Willebrand Factor: Measuring its Antigen or Function? Correlation between the Level of Antigen, Activity, and Multimer Size using Various Detection systems,". *Thromb. Res.*, 91:39-43.

Furlan et al, (1985), "Reactivity of Small Molecular Forms of Human Factor VII/von Willebrand Factor with Botrocetin and Anti-Factor VIII-Coated Latex Particles," *Thromb. Haemost.*, 54(2):463-465.

Galfre et al, (1981), "Preparation of Monoclonal Antibodies: Strategies and Procedures," *Meth. Enzymol.*, 73:3-46.

Harsfalvi et al., (1995), "Calin From Hirudo Medicinalis, an Inhibitor of von Willebrand Factor Binding to Collagen Under Static and Flow Conditions," *Blood*, 85(3):705-711.

Howard et al., (1971), "Ristocetin-A New Tool in the Investigation of Platelet Aggregation," *Thromb. Diath. Haemorrh.*, 26:362-369.

Hoylaerts et al., (1995), "Promotion of binding of von Willebrand factor to platelet glycoprotein Ib by dimers of ristocetin," *Biochem. J.*, 306:453-463.

Hoylaerts et al., (1997), "von Willebrand factor binds to native callagen VI primary via its A1 domain," *Biochem. J.*, 324:185-191.

Ingerslev, (1987), A sensitive ELISA for von willebrand factor (vWf:Ag); *Scand. J. Clin. Lab. Invest.*, 47:143-149.

Köhler et al., (1975), "Continuous cultures of fused cells secreting antibody of predefined specificity," *Nature*, 256:495-497.

Lankhof et al, (1996), "A3 Domain Is Essential for Interaction of von Willebrand Factor with Collagen Type III," *Thromb. Haemost.*, 75:950-958.

Li et al., (2001), "Expression of the Amino-Terminal Domain of Platelet Glycoprotein Ibα: Exploitation of a Calmodulin Tag for Determination of Its Functional Cavity," *Protein Expression and Purification*, 22:200-210.

Macfarlane et al., (1975), "A Method for Assaying von Willebrand Factor (Ristocetin Cofactor)," *Thromb. Diath. Haemorrh.*, 34:306-308.

Marchese et al., (1999), "Adhesive properties of the isolated Amino-terminal domain of platelet glycoprotein Ibα in a flow field," *Proc. Natl. Acad. Sci. USA*, 96:7837-7842.

Merrifield, (1963), "Solid Phase Peptide Synthesis. I. The Synthesis of a Tetrapeptide," *J. Am. Chem. Soc.*, 85:2149-2154.

Meyer et al., (1993), "Expression and Characterization of Functionally Active Fragments of the Platelet Glycoprotein (GP) Ib-IX Complex in Mammalian Cells," *J. Bio. Chem.*, 268(27):20555-20562.

Mohlke et al., (1997), "von Willebrand disease and quantitative variation in von Willebrand factor," *J. Lab. Clin. Med.*, 130:252-261.

Murata et al., (1991), "Site-directed Mutagenesis of a Soluble Recombinant Fragment of Platelet Glycoprotein Ibα Demonstrating Negative Charged Residues Involved in von Willebrand Factor Binding," *J. Biol. Chem.*, 266(23):15474-15480.

Murata et al., (1993), "Expression of Phenotypic Abnormality of Platelet-Type von Willebrand Disease in a Recombinant Glycoprotein Ibα Fragment," *J. Clin. Invest.*, 91:2133-2137.

Murdock et al., (1997), "von Willebrand Factor Activity Detected in a Monoclonal Antibody-based ELISA: an Alternative to the Ristocetin Cofactor Platelet Agglutination Assay for Diagnostic Use," *Thromb. Haemost.*, 78:1272-1277.

Ng et al., (1999), "Imaging Protein Kinase Cα Activation in Cells," *Science*, 283:2085-2089.

Obert et al., (1999), "Conformational Changes in the A3 Domain of von Willebrand Factor Modulate the Interaction of the A1 Domain With Platelet Glycoprotein Ib," *Blood*, 93:1959-1968.

Petersen et al., (1996), "Functional Expression of Single Chain Glycoprotein Ib Alpha on the Surface of COS Cells and BHK Cells," *Thromb. Haemost.*, 76(5):768-773.

Petersen et al., (1992), "Transient Expression of Recombinant Glycoprotein Ibα Polypeptides in COS Cells that Inhibit von Willebrand Factor Binding to the Platelet Glycoprotein Ib/IX Complex," *Thromb. Haemost.*, 68(2):203-207.

Preston, (1998), "Assays for von Willebrand Factor Functional Activity: A UK NEGAS Survey," *Thromb. Haemost.*, 80:863.

Rodeghiero et al., (1987), "Epidemiological Investigation of the Prevalence of von Willebrand's Disease," *Blood*, 69:454-9.

Ruggeri et al., (1983), "Platelets Have More Than One Binding Site for von Willebrand Factor," *J. Clin. Invest.*, 72:1-12.

Sadler, (1994), "A Revised Classification of von Willebrand Disease, For the Subcommittee on von Willebrand Factor of the Scientific and Standardization Committee of the International Society on Thrombosis and Haemostasis," *Thromb. Haemost.*, 71:520-5.

Sakariassen et al., (1983), "A perfusion chamber developed to Investigate platelet interaction in flowing blood with human vessel wall cells, their extracellular matrix, and purified components," *J. Lab. Clin. Med.*, 102:522-535.

Sixma et al., (1991), "Effect of deletion of the A1 domain of von Willebrand factor on its binding to heparin, collagen and platelets in the presence of ristocetin," *Eur. J. Bio. Chem.*, 196:369-375.

Thomas et al., (1994), "Ein einfacher Test für die Bestimmung der Funktion des Von-Willebrand-Faktors: die Kollagenbindungsaktivität," *Hämostaseologie*, 14:133-9. (English abstract provided).

Tomai et al., (1993), "A Monoclonal Antibody Recognizes a von Willebrand Factor Domain within the Amino-terminal Portion of the Subunit that Modulates the Function of the Glycoprotein IB- and IIB/IIIA-binding Domains," *J. Clin. Invest.*, 91:273-282.

Vanhoorelbeke et al., (2000), "A Reliable and Reproducible ELISA Method to Measure Ristocetin Cofactor Activity of von Willebrand Factor," *Thromb. Haemost.*, 83:107-113.

Veyradier et al., (1998), "Laboratory diagnosis of von Willebrand disease," *Int. J. Clin. Lab. Res.*, 28:201-210.

Vicente et al., (1988), "Isolation and Functional Characterization of the von Willebrand Factor-binding Domain Located between Residues $His^1$-$Arg^{293}$ of the α-Chain of Glycoprotein Ib," *J. Bio Chem.*, 263:18473-18479.

Wittmann-Liebold et al, (1994), "Analysis and Characterization of Proteins," *Concepts in Protein Engineering and Design An Introduction* (Wrede Eds.), Walter de Gruyter, Berlin, New York, pp. 1-107.

Sadler, (1998), "Biochemistry and Genetics of von Willebrand Factor," *Annu. Rev. Biochem.*, 67:395-424.

Schumpp-Vonach et al., (1995), "Stable Expression in Chinese Hamster Ovary Cells of a Homogeneous Recombinant Active Fragment of Human Platelet Glycoprotein," *Cytotechnology*, 17:133-141.

Budde et al., "Hämostaseologie, Molekulare und zellulare Mechanismen, Pathophysiologie und Klinik"; Springer Verlag (1998), 228-237 (English abstract attached).

Lechner, "Blutgerinnungsstörungen", Springer Verlag Berlin-Heidelberg-New York, 1982, p. 197-200 (English translation attached).

Vanhoorebeke et al., (2000), "A reliable and reproducible ELISA method to measure ristocetin cofactor activity of von Willebrand factor," Thromb. Haemost., 83:107-113.

Report of the National Institutes of Health, (2007) "The Diagnosis, Evaluation, and Management of von Willebrand Disease."

Lopez, (1994), "The platelet glycoprotein Ib-IX complex," Blood Coag. Fibrin., 5:97-119.

Favaloro (2007), "An updated on the von Willebrand factor collagen binding assay," Semin. Thromb. Haemost., 33:727-744.

\* cited by examiner

DETECTION OF VON-WILLEBRAND FACTOR (VWF) ACTIVITY

This application is a national phase application of the International Application No. PCT/EP00/06345, filed Jul. 5, 2000, which claims benefit of European Application No. 99112867.7, filed Jul. 5, 1999.

The present invention relates to method for detecting von-Willebrand factor (vWF) activity comprising assaying a sample in the presence of a soluble form or portion of glycoprotein Ib($\alpha$) (GPIb($\alpha$)) and ristocetin, or a functionally equivalent substance. Additionally, the invention relates to the use of the aforementioned soluble form or portion of glycoprotein Ib($\alpha$), of ristocetin or a functional equivalent substance, of specifically reacting anti-GPIB($\alpha$) antibody (ies) and/or of specific binding partners, like specifically reacting anti-vWF antibody(ies) for carrying out the method of the invention. Furthermore, the present invention relates to kits for carrying out the method of the invention.

Several documents are cited throughout the text of this specification. Each of the documents cited herein (including any manufacturer's specifications, instructions, etc.) are hereby incorporated by reference; however, there is no admission that any document cited is indeed prior art of the present invention.

Von Willebrand factor (vWF) is a large, multimeric glycoprotein that is present in plasma, subendothelium and platelet $\alpha$-granules. vWF has two distinct functions in primary hemostasis: it promotes platelet adhesion at sites of vascular injury and it protects coagulation factor VIII (FVIII) from inactivation by activated protein C (for review, see: Sadler, Annu Rev Biochem 1998; 67:395-424).

Von Willebrand's disease (vWD) arises from quantitative and qualitative abnormalities in vWF. It is the most common inherited bleeding disorder with a prevalence of 0.1%-1% (Rodeghiero, Blood 1987; 69:454-9). Three major categories of vWD are distinguished (Sadler, Thromb Haemost 1994; 71:520-5). Types 1 and 3 refer to mild and severe quantitative deficiency of vWF respectively, whereas type 2 refers to qualitative abnormalities. Qualitative type 2 vWD is further divided into four subtypes (A, B, M and N). In type 2A individuals, there is an absence of high molecular weight (HMW) multimers. Type 2B variants show an increased affinity for glycoprotein (GP) Ib on platelets resulting in a loss of HMW multimers in plasma. VWD type 2M includes variants in which platelet adhesion is impaired but the vWF multimer distribution is normal. Type 2N variants show a markedly decreased affinity for factor VIII (FVIII). As discussed, inter alia, in Veyradier, Int. J. Clin. Lab. Res. 28 (1998), 201-210, a decreased von Willebrand factor ristocetin cofactor activity/ von Willebrand factor antigen ratio is in favor of the three subtypes (2A, 2M, and 2B) defined by an abnormal interaction between von Willebrand factor and platelet glycoprotein Ib, whereas a decreased factor VIII/von Willebrand factor antigen ratio suggests subtype 2N, defined by a defective binding of von Willebrand factor to factor VIII.

In most laboratories, the basic screening tests used in order to evaluate a new patient suspected suffering from vWD are: bleeding time (BT), vWF antigen (vWF:Ag) level and vWF ristocetin-induced platelet agglutination, termed ristocetin cofactor activity (vWF:RiCof). Additional studies such as determination of vWF:RiCoF at various ristocetin concentrations, ristocetin-induced platelet agglutination with plasma and platelets from the patient, multimer gel analysis and DNA analysis permit further categorization of vWD required for direct and appropriate therapy (Ewenstein, Annu Rev Med 1997; 48:525-42; Veyradier, loc. cit.). Such assays, however, can be performed in highly specialized laboratories only. Determination of the vWF collagen binding activity (vWF: CBA) was also shown to be a valuable tool in diagnosing vWD patients (Brown, Thromb Res 1986; 43:303-11, Favaloro, Blood Coagul Fibrinolysis 1991; 2:285-91).

Due to the limitations of each assay and due to a wide diversity of intraindividual varieties no single test is sufficiently robust to permit detection of all vWD variants. Measurement of the vWF:Ag is most frequently performed as an ELISA assay (Ingerslev, Scand J Clin Lab Invest 1987; 47:143-9). This assay provides good information on the absolute level of vWF present but no information on the quality of the vWF can be obtained. As a result vWF:Ag assay will help detect all type 3, most type 1 and only some type 2 vWD patients, as many type 2 vWD patients will yield vWF:Ag results that are within the normal reference range.

Two vWF-assays do not detect the concentration of vWF (vWF:Ag) only but rather correlate with its functional properties: the vWF:ristocetin cofactor assay and the vWF:collagen binding assay. Since qualitative features/functional properties of the vWF are measured with these assays the terminology "vWF activity" is used for vWF determined by these procedures. In the following the term "vWF activity" is used to describe the ristocetin-dependent interaction between GPIb($\alpha$) (or a fragment) thereof and vWF.

Ristocetin is an antibiotic that promotes the interaction between the platelet GP Ib/V/IX complex and vWF (Howard, Thromb Diath Haemorrh 1971; 26:362-9; Hoylaerts, Biochem J 1995; 306:453-63). This co-factor-activity of ristocetin is observed primarily in the presence of HMW forms of vWF (Fischer, Thromb Res 1996; 84:55-66; Federici, Br J Haematol 1989; 73:93-9). The region of GPIb involved in this interaction has been identified to the amino terminal 42 kDa globular part of GPIb$\alpha$ (Vincente, J. Biol Chem 1988, 263: 18473-18479).

The vWF:RiCoF activity is determined by using a platelet agglutination procedure (Macfarlane, Thromb Diath Haemorrh 1975; 34:306-8). Dilutions of patient platelet-poor plasma are mixed with washed para-formaldehyde-fixed platelets in the presence of a fixed concentration of ristocetin and the ability of the patient plasma to induce platelet agglutination is measured. The vWF:RiCof assay permits the identification of type 2A and 2B patients as low levels of vWF: RiCof relative to vWF:Ag are measured. This assay however has both high inter-assay and high inter-laboratory variability due to the complexity of the procedure e.g. the use of donor platelets, the different testing steps and the sometimes difficult interpretation of the platelet agglutination (Favaloro, Pathology 1997; 29:385-91). It is known that the high variability in the vWF:RiCof assay can lead to a misdiagnosis of vWD. Furthermore, the high variability of the vWF:RiCof assay may be due to the rather complex system used, i.e. the employment of whole platelets.

The platelet-based vWF-assays are jeopardized by the fact that platelets have more than one binding site for vWF (Ruggeri, J. Clin. Invest. 1983; 72: 1-12) which comprise, inter alia, the GPIIb/IIIa complex (De Marco, J. Clin. Invest. 1986; 77: 1272-1277). Additionally, vWF is known to bind to other biological (macro) molecules like proteins and modified lipids, which comprise not only Factor VIII and (fibrillar) collagens, but also heparins, glycosaminoglycans and sulfatides (see, e.g., Mohlke, J. Lab Clin Med 1997, 130: 253-261). It is further known that binding of vWF to the subendothelium induces a conformational change that allows primary interaction with GPIb, the latter generating a signal for platelet activation upon which the vWF binds (mediated by the RGD domain to GPIIb/IIIa) a complex on said activated platelet.

Like GPIb, the GPIIb/IIIa complex is an integral component of the platelet membrane which is thought to be essential for normal adhesion and aggregation (see, e.g., Berliner, J Biol Chem 1988, 263:7500-7505). As Lechner ("Blutgerinnungsstörungen", Springer Verlag Berlin-Heidelberg-New York, 1982, p. 197-200) describes, the preparation of platelets to be used in vWF:RiCoF assays leads to an activation of said platelets. Therefore, whole platelets, as commonly used in vWF:RiCoF assays, comprise more than one binding molecule for vWF. As pointed out herein above, the interaction between vWF and platelets is rather complex and depends on at least two different receptors on the platelets as well as on the physiological properties of vWF (e.g., HMW multimers). Several attempts have been undertaken to further standardize and simplify the vWF:RiCof activity test but the difficulties in interpretation of the platelet agglutination assays remains. The vWF:CBA assay is a functional assay in which the quality of the protein is measured (Brown, Thromb Res 1986; 43:303-11; Favaloro, Blood Coagul Fibrinolysis 1991; 2:285-91). The vWF:CBA is determined in an ELISA based procedure in which primarily HMW multimers are detected (Fischer, Thromb Res 1996; 84:55-66; Aihara, Thromb Haemost 1988; 59:485-90). This test also contributes to the diagnosis of type 2A and type 2B patients as these subtypes tend to give very low vWF:CBA values due to the absence of HMW vWF forms in the plasma of such patients. The vWF:CBA test, however, is not a routine test in vWD diagnosis and is measuring a different property of vWF as compared to the vWF:Ricof test. Another disadvantage of the vWF:CBA assay is the high sensitivity to transport influences and repeated freezing/thawing cycles (as, inter alia, mentioned in Budde, "Hämostaseologie, Molekulare und zellulare Mechanismen, Pathophysiologie und Klinik"; Springer Verlag (1998), 228-237).

Furthermore, current tests for von-Willebrand's disease (vWD) are usually based on the above described assays, like bleeding time, vWF antigen and vWF ristocetin cofactor activity (employing platelet aggregating activity in the presence of ristocetin). Often, platelet-based assays not only show relatively poor sensitivity and reproducibility, but require also drawing of fresh blood samples and are time consuming (Murdoch, Thromb. Haemost. 78 (1997), 1272-1277). These tests are known to be non-accurate, non-reproducible and often fail to define the disorder (as reviewed, inter alia, in Mohlke, J. Lab. Clin. Med. 130 (1997), 252-260). Additionally, Favaloro (Am. J. Clin. Pathol. 104 (1995), 264-271) found that clinical use of different assays inconsistently predicted vWD diagnosis. Thus, the above described assays for detecting vWD are suboptimal or are not amenable to the analysis of a large number of samples (e.g. DNA-and multimer analysis).

The technical problem underlying the present invention was to provide improved means for a more reproducible and more precise test for von-Willebrand factor with a low inter- and intra-assay variability. The solution to said technical problem is achieved by providing the embodiments characterized in the claims.

Accordingly, the present invention relates to a method for detecting von-Willebrand factor (vWF) activity comprising assaying a sample in the presence of (a) a soluble form or portion of glycoprotein Ib($\alpha$) (GPIb($\alpha$)) and (b) ristocetin, or a functionally equivalent substance.

In accordance with the present invention, it has been surprisingly found that von-Willebrand factor activity can be precisely and reproducibly be assayed in a convenient manner by assaying a sample from a patient known or suspected to suffer from von-Willebrand's disease or by assaying a sample obtained from a healthy individual. The assay system of the present invention is less complex than the above-referenced vWD/vWF assays and surprisingly still yield clinically relevant data which, in some respects, can be used to substitute platelet based vWF:RiCof assays.

As pointed out herein above, the term "vWF activity" as used in accordance with this invention describes the ristocetin-dependent interaction between GPIb ($\alpha$) (or a fragment thereof) and vWF.

Generally, the invention as outlined above envisages the employment of a soluble form, portion or fragment of glycoprotein Ib($\alpha$). The term "soluble form or portion of glycoprotein Ib($\alpha$)" as used herein denotes a molecule, preferably a protein, a peptide or a (poly)peptide which is not associated with platelets. Furthermore, said term comprises fragments of said glycoprotein GPIb($\alpha$), inter alia, the extra-cellular part of said protein. Within the scope of the present invention are furthermore soluble forms, portions or fragments of GPIb($\alpha$) which may comprise, besides proteinaceous parts, specific carbohydrates. Such GPIb ($\alpha$), portions or fragments thereof may be obtained by biochemical or synthetic methods and/or techniques of recombinant molecular biology. Such methods are known to those of ordinary skill in the art (see, e.g., Sambrook et al. "Molecular Cloning; A Laboratory Manual", $2^{nd}$ Edition, Cold Spring Harbour Laboratory Press, Cold Spring Harbour, N.Y. (1989); Harlow and Lane "Antibodies, A Laboratory Manual", CSH Press, Cold Spring Harbor, N.Y. (1988); Merrifield, J. Am. Chem. Soc. 85 (1963), 2149-2146; Stewart, "Solid Phase Peptide Synthesis", WH Freeman Co, San Francisco (1969); Scopes, "Protein Purification", Springer Verlag, New York, Heidelberg, Berlin (1987); Janson, "Protein Purification, Principles, High Resolution Methods and Applications", VCH Publishers, New York, Weinheim, Cambridge (1989); Wrede, "Concepts in Protein Engineering and Design", Walter de Gruyter, Berlin, N.Y. (1994); Wittmann-Liebold, Jungblut "Analysis and Characterization of Proteins", 47-107).

In addition to recombinant or biochemical production, said GPIb($\alpha$), portion(s) or fragment(s) thereof may be produced by direct peptide synthesis using solid-phase techniques (cf Stewart et al. (1969) Solid Phase Peptide Synthesis, WH Freeman Co, San Francisco; Merrifield, J. Am. Chem. Soc. 85 (1963), 2149-2154). In vitro protein synthesis may be performed using manual techniques or by automation. Automated synthesis may be achieved, for example, using Applied Biosystems 431A Peptide Synthesizer (Perkin Elmer, Foster City Calif.) in accordance with the instructions provided by the manufacturer. Various portions or fragments of GPIb($\alpha$) may be chemically synthesized separately and combined using chemical methods to produce the full length molecule.

Within the scope of this invention are therefore all forms of GPIb($\alpha$) and/or fragments thereof which are not associated with or bound to platelets. Preferably, said soluble form, portion or fragment of glycoprotein Ib($\alpha$) comprises the N-terminal domain of the $\alpha$ chain of human platelet glycoprotein Ib, even more preferably, it comprises the N-terminal 42 kDa part of GPIb($\alpha$) and most preferably it comprises the residues His 1-Val 289 (see, e.g., Schampp-Vonach, Cytotechnology 17 (1995) 133-141). The term "soluble form or portion of GPIb($\alpha$)" comprises, within the scope of this invention, not only single, individual molecules, but also larger complexes, such as, e.g., at least two GPIb($\alpha$) molecules which may form a single entity.

The term "ristocetin or a functionally equivalent substance" as used in accordance with this invention means the glycopeptide antbiotic isolated from Nocardia lurida, which mimics the active constituent(s) of the exposed vessel wall and causes the binding of human vWF to human platelets and platelet agglutination. Furthermore, the term comprises recombinantly or biochemically produced ristocetin or fragments thereof. Additionally, the term "functionally equivalent substances" comprises any substance which can replace ristocetin or fragments thereof as a non-physiological inducer of binding of vWF to GPIb. (Furlan, 1995, Thromb. Haemost. 54: 463-465). Within the scope of the invention is furthermore the use of specific antibodies that enhance the efficacy/potency of ristocetin which, in turn, allow the use of lower ristocetin concentrations (see e.g. Tornai, J Clin Invest 1993; 91:273-282).

In a more preferred embodiment, the method of the present invention comprises a method wherein said detection is carried out by detecting the formation of a complex of vWF and GPIb($\alpha$) and/or a formed complex of vWF and GPIb($\alpha$). The detection of the formation of said complex and/or the detection of the formed complex may be carried out by methods known to the person skilled in the art. Examples of such detections are described herein below.

In order to detect said complex or said formation of a complex between GPIb ($\alpha$) and vWF, proteins, like GPIb ($\alpha$), preferably labelled, as well as different antibodies, like anti-GPIb ($\alpha$), anti-vWF or anti-factor VIII antibodies might be employed. Furthermore, it is envisaged that Factor VIII, collagen(s) and/or GPIIb/IIIa can be used to detect said complex or complex formation.

In one embodiment of the present invention said GPIb($\alpha$) or the above mentioned complex formed by vWF and said soluble form or portion of GPIb($\alpha$) is bound to a solid support.

Suitable methods for binding said GPIb($\alpha$) or said complex to the solid support include, but are not limited to ionic, hydrophobic, covalent interactions and the like. The solid support can retain one or more additional receptor(s) which has/have the ability to attract and immobilize said GPIb($\alpha$) molecule(s) or said complex. These receptors can comprise a charged surface that is oppositely charged with respect to said GPIb($\alpha$) molecule(s) or said complex or to a charged substance conjugated to the capture reagent or the receptor can be any specific binding partner, such as, inter alia, an antibody. This means said binding includes chemical, biochemical coupling, coating, attachment by von-der-Waals forces etc. The binding of said complex can be mediated, inter alia, by anti-GPIb$\alpha$ antibodies, by anti-vWF antibodies, by anti-factor VIII antibodies as well as by collagen(s), factor VIII and/or GPIIb/IIIa.

It is preferred that said GPIb($\alpha$) is bound to said solid support by a specifically reacting anti-GPIb($\alpha$) antibody and/or that said complex is bound to said support by a specifically reacting anti-GPIb($\alpha$) antibody, by a specifically reacting anti-vWF antibody, by a specifically reacting anti-Factor VIII antibody and/or by collagen. Specifically, reacting antibodies, for example, against GPIb($\alpha$) or fragments thereof are known in the art and are described, inter alia, in the appended examples (e.g., example 1).

Antibodies specifically reacting with Factor VIII are also known in the art and comprise, inter alia, the antibody described in Casonato Am J Clin Path 1998; 109: 347-352. Useful collagen(s) has/have been described, inter alia, in Brown, Thromb. Res. 1986, 43:303-11; Favaloro, Blood Coag. Fibrinol. 1991; 2:285-91 or Thomas, Hamostaseologie 1994; 14:133-9.

In a further preferred embodiment of the method of the present invention, said detection is carried out by a specifically reacting anti-vWF antibody, by a specifically reacting anti-Factor VIII antibody, by a specifically reacting anti-GPIb ($\alpha$) antibody, by collagen and/or mixture thereof. Polyclonal anti-vWF antibodies are known in the art and are, inter alia, available from Serotec Ltd. (AHPO62, MCA127).

Comprised by the method of the invention are also embodiments wherein the above referenced antibody/antibodies is (are) (a) monoclonal antibody/antibodies, (a) polyclonal antibody(ies) or (a) chimeric antibody(ies). Furthermore, said antibody(ies) comprise(s) synthetic antibodies, antibody fragments, or a chemically modified derivative of any of these.

Monoclonal antibodies can be prepared, for example, by the techniques as originally described in Köhler and Milstein, Nature 256 (1975), 495, and Galfré, Meth. Enzymol. 73 (1981), 3, which comprise the fusion of mouse myeloma cells to spleen cells derived from immunized mammals with modifications developed in the art.

As mentioned herein above, the antibodies can be monoclonal antibodies, polyclonal antibodies or synthetic antibodies as well as fragments of antibodies, such as Fab, Fv or scFv fragments etc. Antibodies or fragments thereof can be obtained by using methods which are described, e.g., in Harlow and Lane "Antibodies, A Laboratory Manual", CSH Press, Cold Spring Harbor, 1988. The production of chimeric antibodies is described, for example, in WO89/09622.

In a further embodiment of the present invention said antibody or said collagen, being used in the detection step of the method of the invention, is (are) detectably labeled. Said label may be, inter alia, a tag, a fluorescent marker, an enzyme, a particle or a radioactive marker. Such labels are well known to the person skilled in the art and comprise, inter alia, horse radish peroxidase, alkaline phosphatase, $\beta$-galactosidase, fluorochromes (like fluorescein, rhodamine, Texas Red, etc.), colloidal metals (like gold particles), biotin, digoxygenin and chemi- or bioluminescent compounds. Any detection method for detecting GPIb($\alpha$) or a fragment thereof, the von-Willebrand factor (vWF) activity, the vWF protein(s) or the presence of a formed complex of vWF and GPIb($\alpha$) or the formation of said complex may be assisted by computer technology. Detection methods can therefore be automated by various means, including image analysis of flow cytometry. For example, in accordance with the present invention, said detection can be carried out by an heterogeneous or by an homogeneous assay or by other detection methods known in the art. These assays and detections comprise, but are not limited to, immuno assays and immuno detections. According to the present invention, said heterogeneous (immuno) assays comprise, inter alia, enzyme linked immunoassays (ELISA), radioimmunoassays (RIA), immuno radio metric assays (IRMA), fluorescent immunoassays (FIA), chemiluminescent immuno assays (CLIA) and/or electro chemiluminescent immuno assays (ECL).

Homogeneous assays comprise assays wherein the binding partners remain in solution. These homogeneous assays, therefore, comprise also agglutination assays which measure the formation of a complex, either a complex without the mediation of an antibody or antibody fragments (homogeneous assay) or a complex formation involving, e.g., a bridging- or detection-antibody (homogeneous immunoassay). An example of such a homogeneous assay is the latex enhanced turbimetric (immuno) assay. Additionally, vWF/vWF activity can be detected, inter alia, by fluorescence resonance energy transfer (FRET), as, e.g., described in Ng, Science 283 (1999), 2085-2089. Aggregation may be recorded by commercially available devices, such as aggregometers.

In accordance with the present invention it might be envisaged that either the direct interaction of the soluble form or portion of glycoprotein Ib(α) with vWF can be directly measured or that one of the complex partners (or both) are bound to the above described solid supports, such as, inter alia, latex beads, and that the interaction/agglutination of said solid support is measured.

In yet another embodiment the solid support of the method of the present invention comprises a plastic, a glass, a silicon, a colloidal metal, a cellulose and/or a polymeric support. Said solid support is selected from the group consisting of solid organic polymers, cellulose/cellulose-based membranes, colloidal metal particles, plastic surfaces, or any combination thereof.

A number of supports known in the art are suitable for serving the purposes of the present invention. Such supports may comprise, inter alia, membranes, plates, stripes, wells, microchips or containers. Suitable materials for such supports or materials for further coating of said supports include, but are not limited to, glass, polystyrene, polyvinyl chloride, polypropylene, polyethylene, polycarbonate, dextran, nylon, amyloses, natural and modified celluloses, like nitrocellulose, polyacrylamide, agaroses, magnetide and metals. The above mentioned colloidal metal particle may be, inter alia, a gold particle, and said above mentioned plastic surface comprises the well of a microtiter plate. Additionally, said above mentioned solid organic polymer comprises a latex bead. Combinations of several supports, such as, e.g., latex beads and colloid metal particles, are also within the scope of the present invention.

As pointed out herein above, the method of the present invention comprises furthermore a method wherein said homogeneous assay is an agglutination assay.

In a more preferred embodiment, the invention relates to a method wherein said agglutination assay is based on agglutination of latex beads. Within the scope of the present invention are, however, also agglutination assays based on agglutination of proteins and/or protein fragments which might be measured, inter alia, turbidometrically. In a yet more preferred embodiment said agglutination is measured by electric field variation, magnetic field variation, turbidimetric variation or light scattering. Such methods are well-known to the skilled artisan.

Therefore, in the method of the present invention, said detection of complex formation between the soluble form or portion of GPIb(α) and vWF can be established by measuring the distinct chance of physical properties which is caused, e.g., by agglutination. Said agglutination can be mediated by direct interaction of the two binding partners and/or may be mediated and effected by (cross) linking one of the binding partners prior or during said detection to a solid support, such as a bead, preferably a latex bead or a colloidal gold particle.

In a particularly preferred embodiment, the sample to be assayed in the present invention is a blood sample. Therefore, said sample is or can be derived from blood, serum or plasma. In a preferred embodiment said blood sample is a plasma sample. The sample to be analyzed may be treated such as to extract, inter alia, proteinaceous components comprising, e.g. proteins, protein fragments or peptides. Furthermore said sample may be diluted.

In a preferred embodiment, said (blood) sample is diluted. Said dilution might be in the range of 1:2 to 1:1,000. Preferably, said dilution is in a range of 1:5 to 1:100. As, inter alia, illustrated in the appended examples, in yet another embodiment the present invention relates to a method for the discrimination between von Willebrand disease (vWD) type 1 and type 2 comprising the steps of (a) detecting vWF activity in a test sample according to the method of the present invention;
(b) determining the amount of vWF-antigen in said test sample;
(c) determining the ratio between vWF activity and vWF-antigen for said test sample; and
(d) comparing the under (c) obtained ratio to the range of ratios established as a normal range.

The term "discrimination" means, within the scope of this invention that patients suffering from vWD can be conveniently classified into patients suffering from type 1 and patients suffering from type 2 vWD employing the method of the present invention. Type 1 vWD-patients are characterized by a normal ratio of vWF:RiCof (vWF activity) to vWF: Ag (vWF-antigen), whereas in type 2 patients in below the reference or normal range (determined, e.g., with healthy volunteers). A reduction of vWF:RiCof activity is, accordingly, typical for type 2 patients.

The term "normal range" as used in accordance with this invention is known by the skilled artisan, like physicians, and comprises the term "reference range". "Normal or reference range" is usually determined by measuring the clinical parameter under investigation in a group of subjects considered healthy, but who are otherwise statistically not different in relevant demographic data to patients suspected of having the disease. The values obtained are evaluated by standard statistical procedures and the normal or reference range is then defined, e.g., by covering the range between the mean value±two or three standard deviations.

Preferably, the tested sample from a vWD patient is a plasma sample.

In yet another embodiment, the present invention relates to the use of a soluble form or portion of glycoprotein Ib(α) (GPIb(α)) for carrying out the method of the present invention.

In addition, the present invention relates to the use of ristocetin or a functional equivalent substance for carrying out the method of the present invention.

In a preferred embodiment, the present invention relates to the use of a specifically reacting anti-GPIb(α) antibody and to the use of a specifically reacting anti-vWF antibody for carrying out the method of the present invention.

Furthermore, the present invention relates to the use of a kit for carrying out the method of the present invention, said kit comprising at least one of the following:
(a) a soluble form or portion of glycoprotein Ib(α) (GPIb(α));
(b) ristocetin or a functional equivalent substance;
(c) an antibody as defined herein above; or
(d) a solid support as defined herein above.

In a preferred embodiment, the present invention relates to a kit comprising at least one of the following:
(a) a soluble form or portion of glycoprotein Ib(α) (GPIb(α));
(b) ristocetin or a functional equivalent substance;
(c) an antibody as defined herein above; or
(d) a solid support as defined herein above, adapted for carrying out the method of the present invention, optionally further comprising a standard and/or means for homogeneous or heterogeneous (immuno)assays. The kit of the present invention is particularly useful in carrying out the method of the invention that has been described in detail herein above.

The kit of the invention may comprise a carrier means being compartmentalized to receive in close confinement one or more container means such as vials, tubes and the like, each of the container means comprising one of the separate elements to be used in the method of the invention. For example, one of the containers may comprise, inter alia, the soluble form or portion of GPIb(α) in lyophilized form or in solution. In addition, the carrier means may also contain a plurality of containers each of which comprises, inter alia, different, pre-determined amounts of vWF or of a vWF amount being diagnostic for different types of von-Willebrand disease useful in the method of the invention. These latter containers can then be used to prepare a standard curve into which can be interpolated the results obtained from the sample containing the unknown amount of vWF and/or unknown type of vWF activity.

Additionally, the present invention relates to the method, the use or the kit of the present invention, wherein said soluble form or portion of glycoprotein Ib(α) (GPIb(α)) is recombinantly produced.

Said recombinantly produced GPIb(α) is a peptide or a (poly)peptide. The term (poly)peptide, as mentioned herein above and in accordance with this invention, may comprise naturally occurring peptides or proteins, as well as synthetic or recombinantly produced peptides/proteins. The (poly)peptide may encompass amino acid chains of any length, wherein the amino acid residues are linked by covalent peptide bonds. However, peptidomimetics of such (poly)peptides wherein amino acid(s) and/or peptide bond(s) have been replaced by functional analogs are also encompassed by the invention. In accordance with this invention, a (poly)peptide may comprise different (poly)peptide species. A (poly)peptide species is defined by its chemical composition and modifications of said peptide(s)/polypeptide(s) by, inter alia, glycosylations, acetylations, phosphorylations, lipidations or by amino acid exchanges. The term (poly)peptide species is therefore defined as the smallest unit of protein classification, defined by its chemical structure.

The figures show:

FIG. 1: Ristocetin induced binding of plasma vWF to rGPIbα-fragment (His1-Val289)

Binding of plasma vWF (1/32 to 1/512) to captured rGPIbα-fragment was studied in the presence of 1 mg/ml (■), 760 μg/ml (•), 500 μg/ml (Δ) and 250 μg/ml (∇) ristocetin. In the absence of ristocetin, no binding was observed (not shown).

FIG. 2: Ristocetin induced binding of vWF to rGPIbα-fragment in the presence of anti-GPIb-mAbs and anti-vWF-mAbs A. rGPIbα-fragment was preincubated for 30 min with serial dilutions of mAb 6B4 (■) (an anti-GPIb-mAb inhibiting the ristocetin-induced human platelet agglutination) and mAb 7D2 (•) (a non-inhibitory anti-GPIb-mAb). Next, a constant amount of plasma pool was added (0.032 U/ml, final concentration) and the bound vWF was detected with anti-vWF-Ig-HRP.

B. Constant amounts of plasma pool (0.032 U/ml vWF, final concentration) were preincubated for 30 min with mAb 1C1E7 (12.5 μg/ml, final concentration) (•) before the samples were added to the rGPIbα fragment. The vWF-GPIb binding was studied in the presence of different concentrations of ristocetin and was compared to the binding in the absence of mAb 1C1E7 (■).

C. Plasma pool vWF (0.032 U/ml vWF, final concentration) was preincubated for 30 min with serial dilutions of mAb 701 (■) (an anti-(vWF A1 domain)-mAb inhibiting the ristocetin-induced human platelet agglutination) and mAb 82D6A3 (•) (an anti-(vWF A3 domain)-mAb inhibiting the vWF-collagen binding). Next, the samples were added to the rGPIbα-fragment containing wells, and the bound vWF was detected with anti-vWF-Ig-HRP. The binding curves are representative of 2 experiments.

Figure 2A:
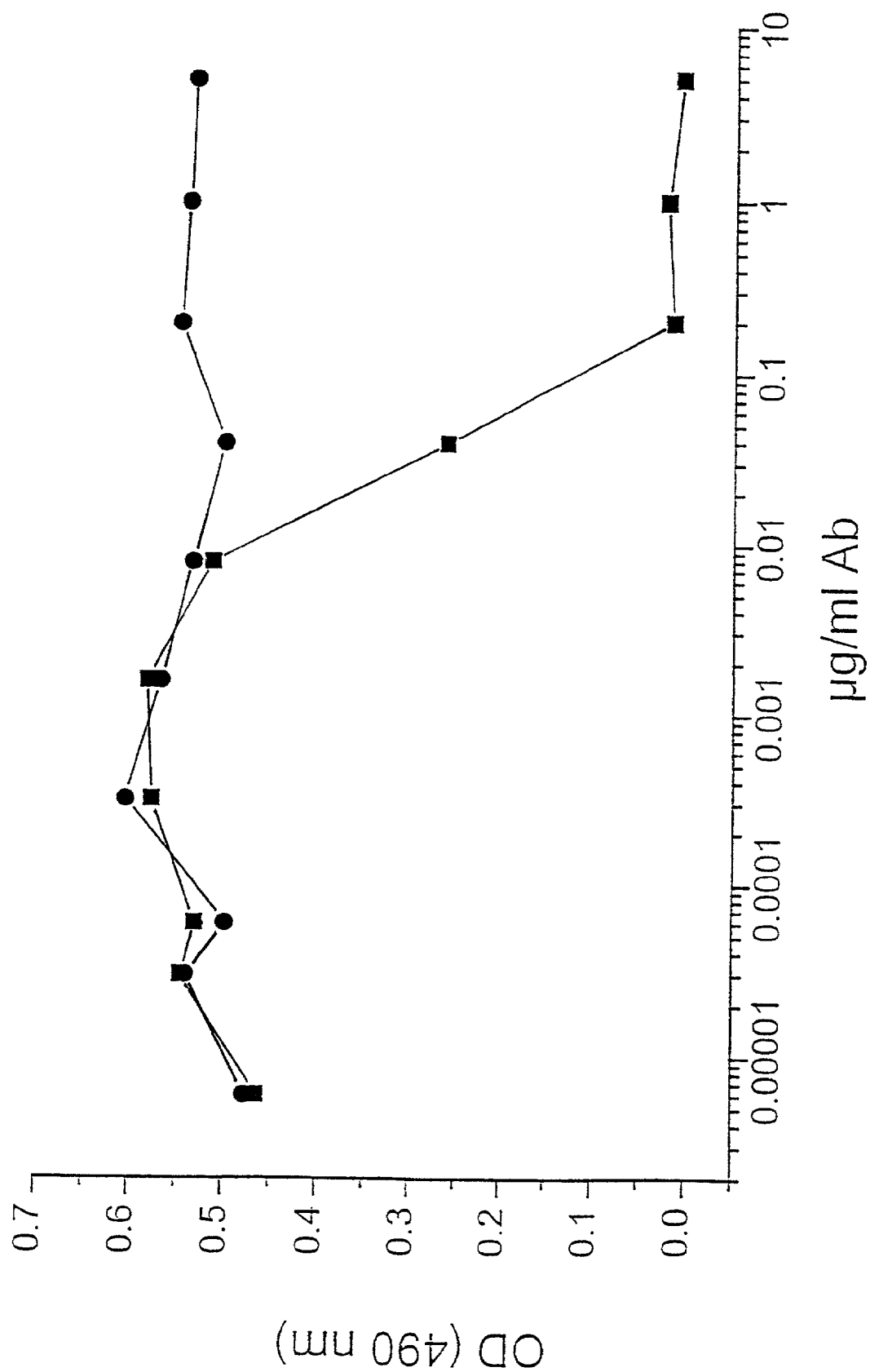
Figure 2B:
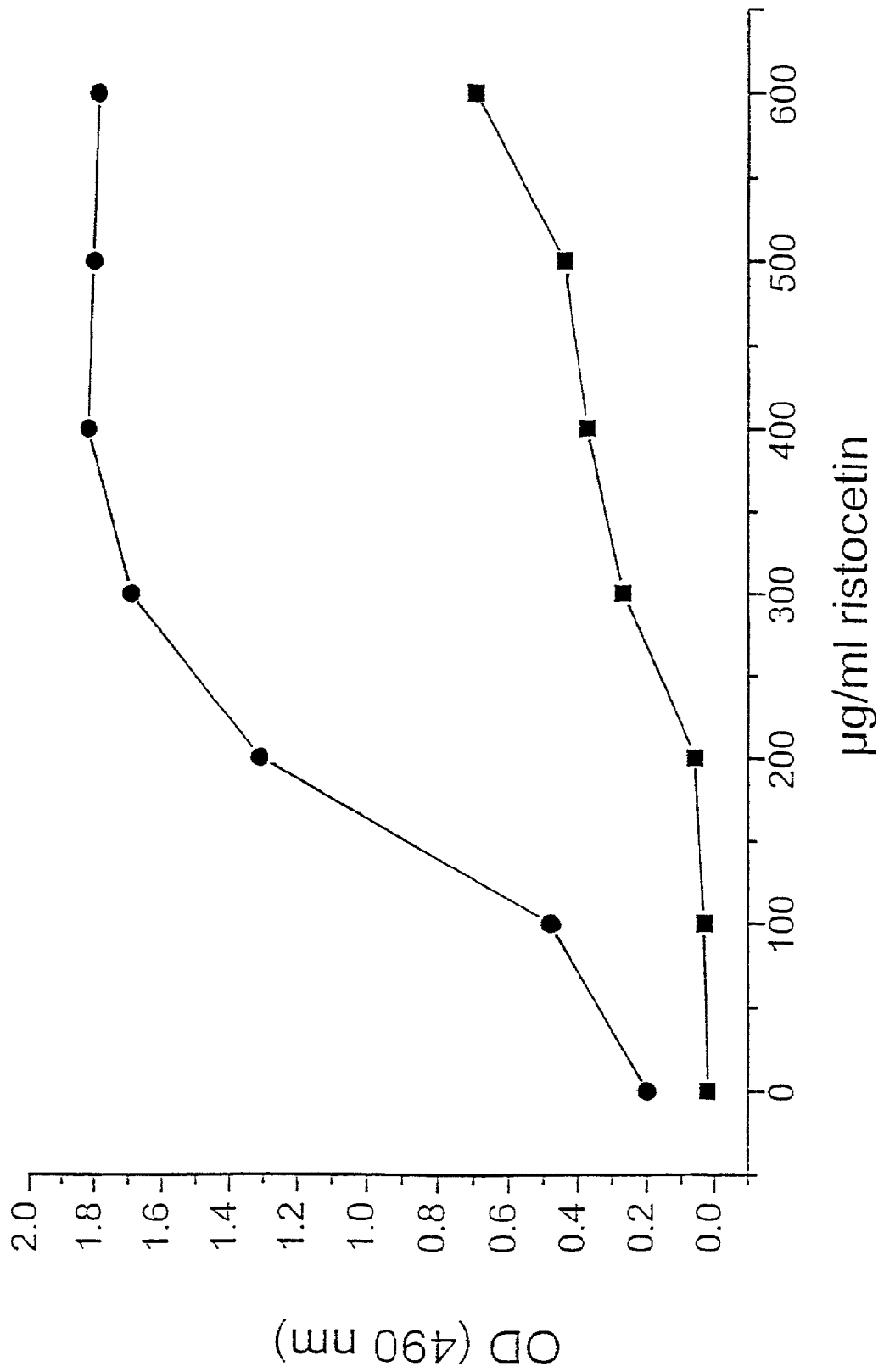
Figure 2C:
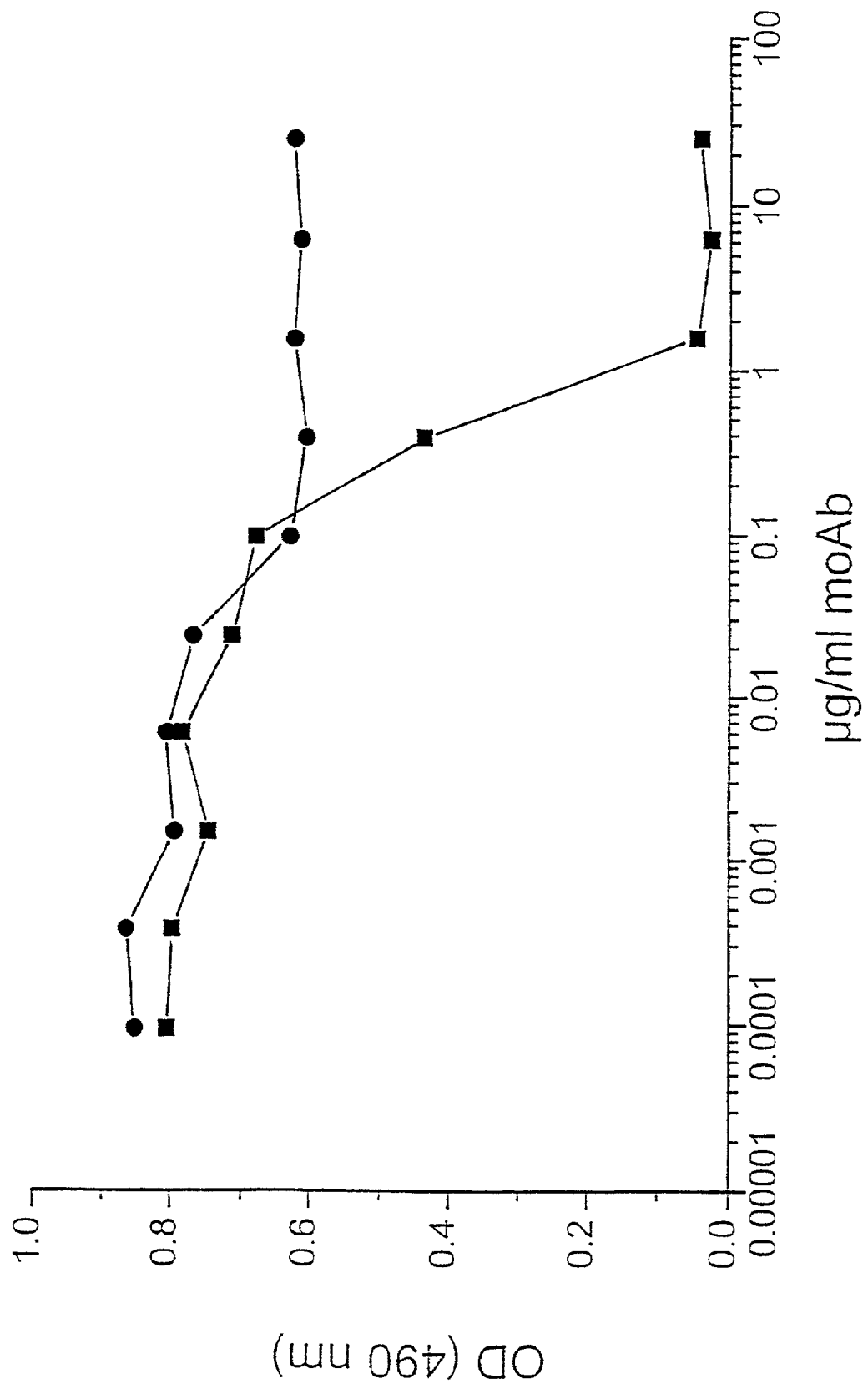
Figure 2D:
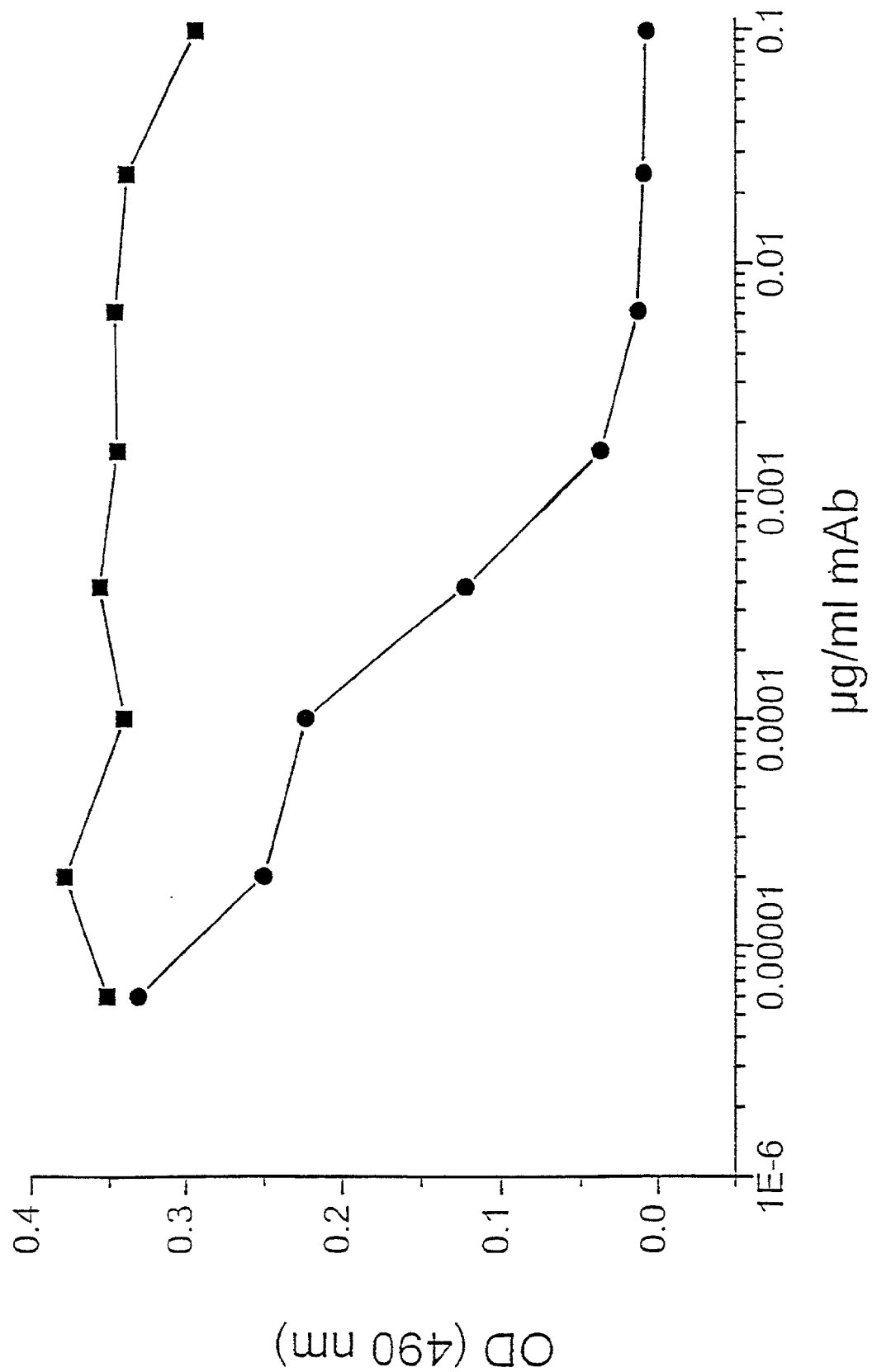

FIG. 2D: vWF binding to human type I collagen in the presence of anti-vWF-mAbs

Plasma pool vWF (0.032 U/ml vWF, final concentration) was preincubated for 30 min with serial dilutions of mAbs 701 (■) and 82D6A3 (•). Next, the samples were added to the collagen coated wells, and the bound vWF was detected with anti-vWF-Ig-HRP.

Figure 3:
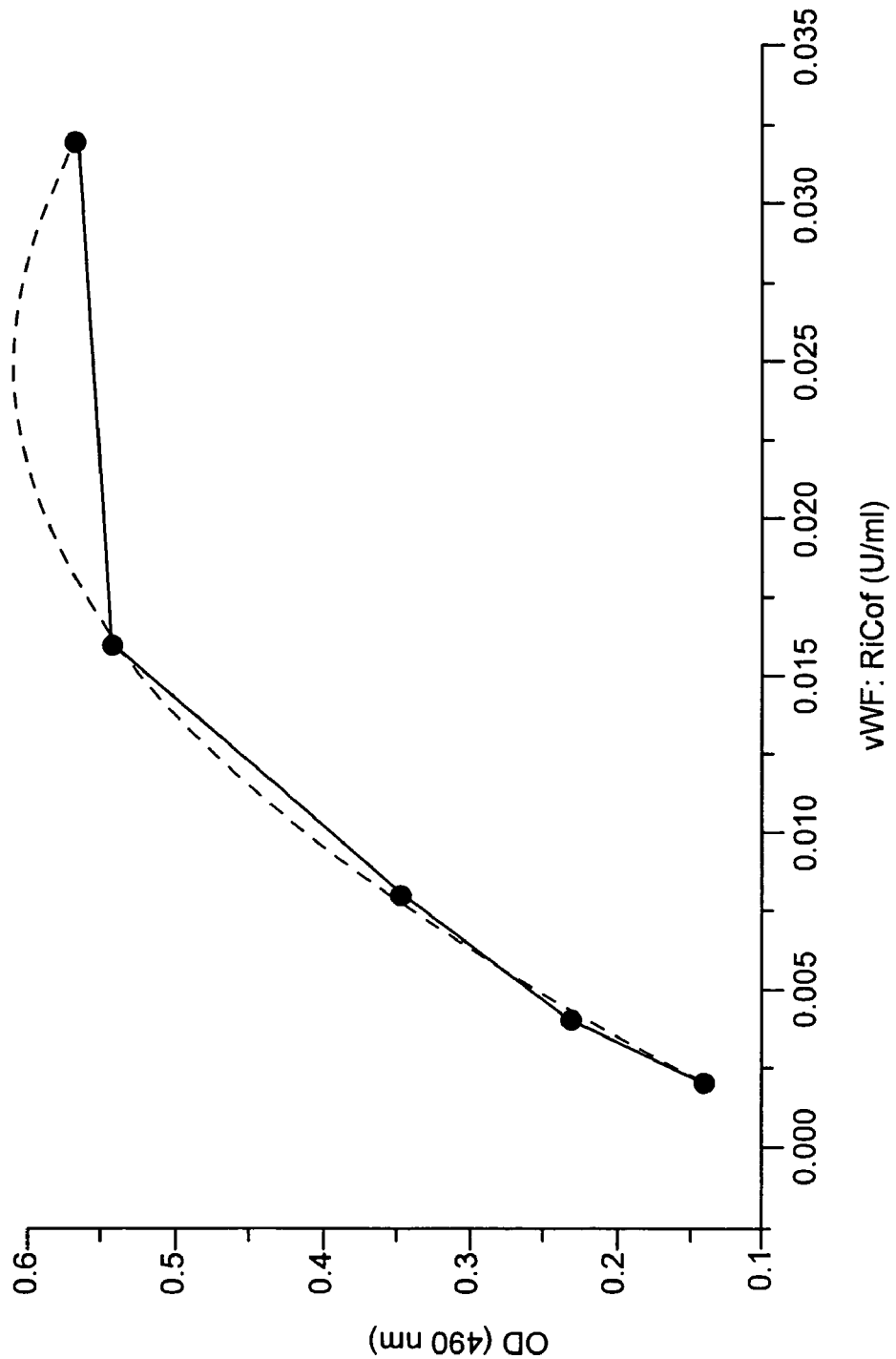

FIG. 3: A representative of a binding curve of plasma pool vWF to the rGPIbα to determine unknown vWF:RiCof activities Polynomial regression (dashed line) was performed on the binding curve of plasma vWF to the rGPIbα-fragment in the presence of 760 μg/ml (•) and resulted in a correlation of 0.9997.

Figure 4:
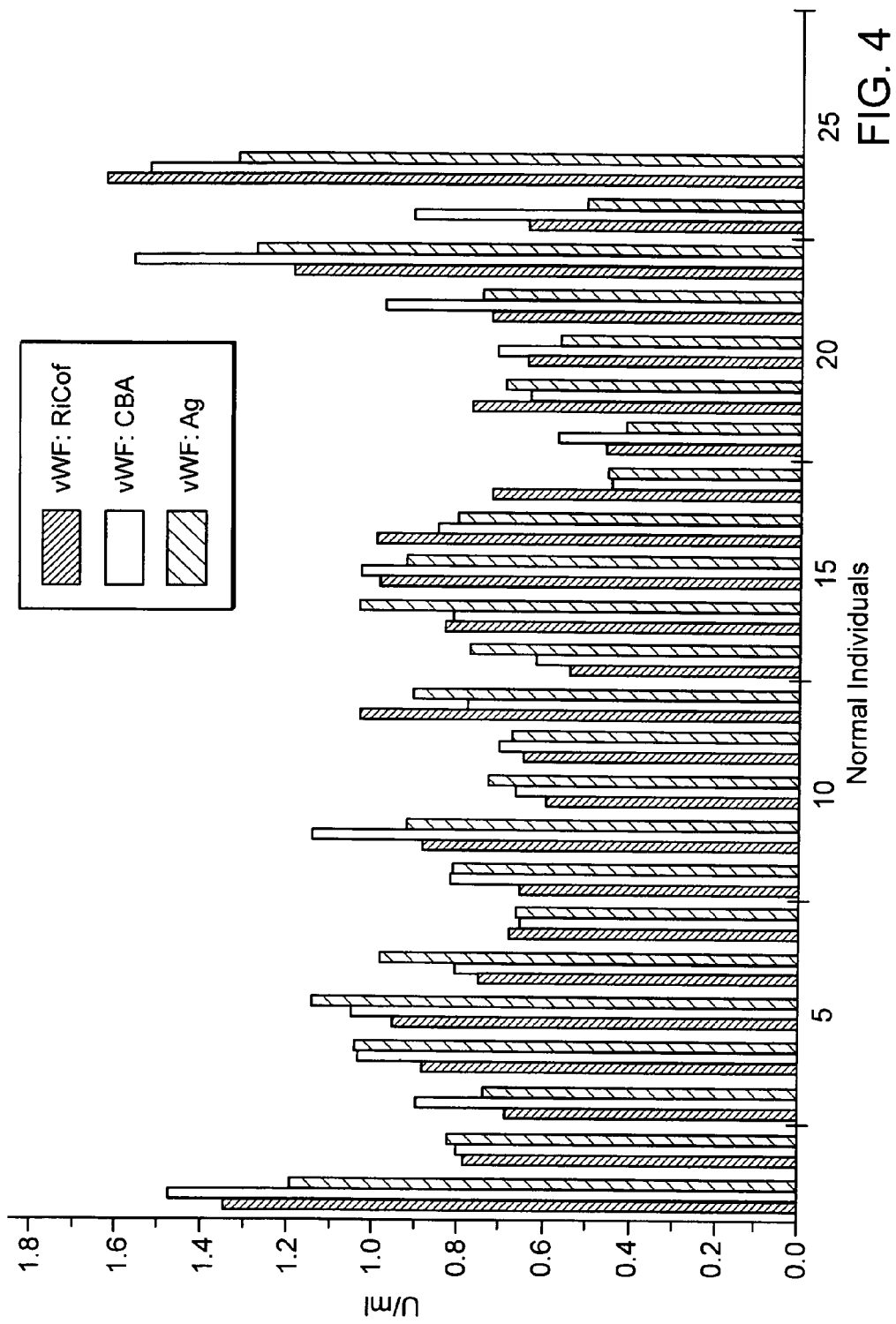

FIG. 4: vWF:RiCof, vWF:CBA and vWF:Ag of plasma vWF from normal individuals (n=24)

vWF:RiCof, vWF:CBA and vWF:Ag were determined in ELISA assays (see Materials and Methods). Each data represents the mean of 2 measurements.

Figure 5:
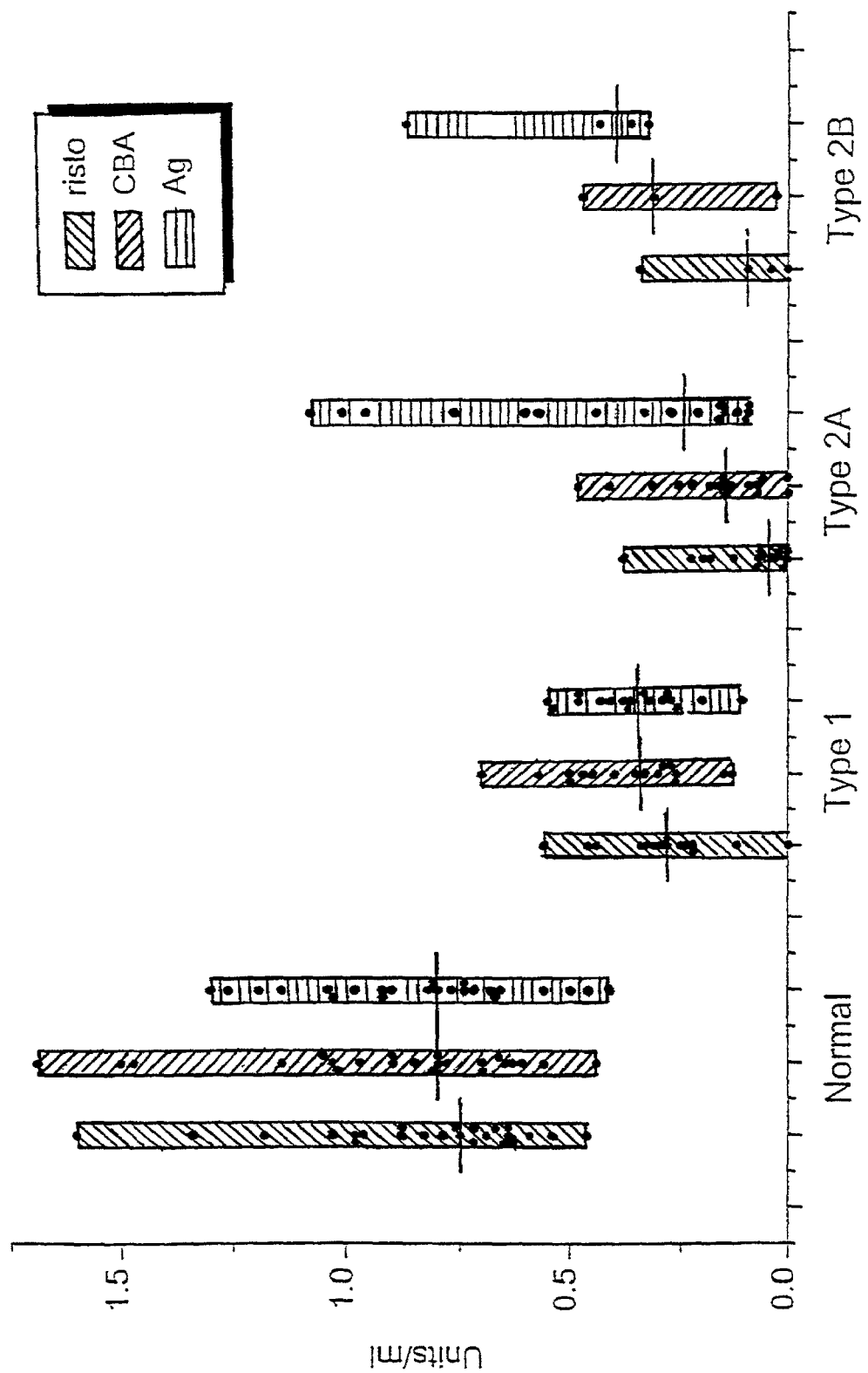

FIG. 5: vWF:RiCof, vWF:CBA and vWF:Ag of plasma vWF from vWD patients

Columns represent a range of data (minimum value to maximum value), containing the individual data points (•). Median values are represented by a horizontal line. Normal individuals (n=24), type 1 vWD patients (n=17), type 2A patients (n=18) and type 2B patients (n=4) are represented, for type 3 (n=3) and type 2N vWD patients (n=2), see text. For each patient all three activities were measured at least 2 times.

Figure 6:
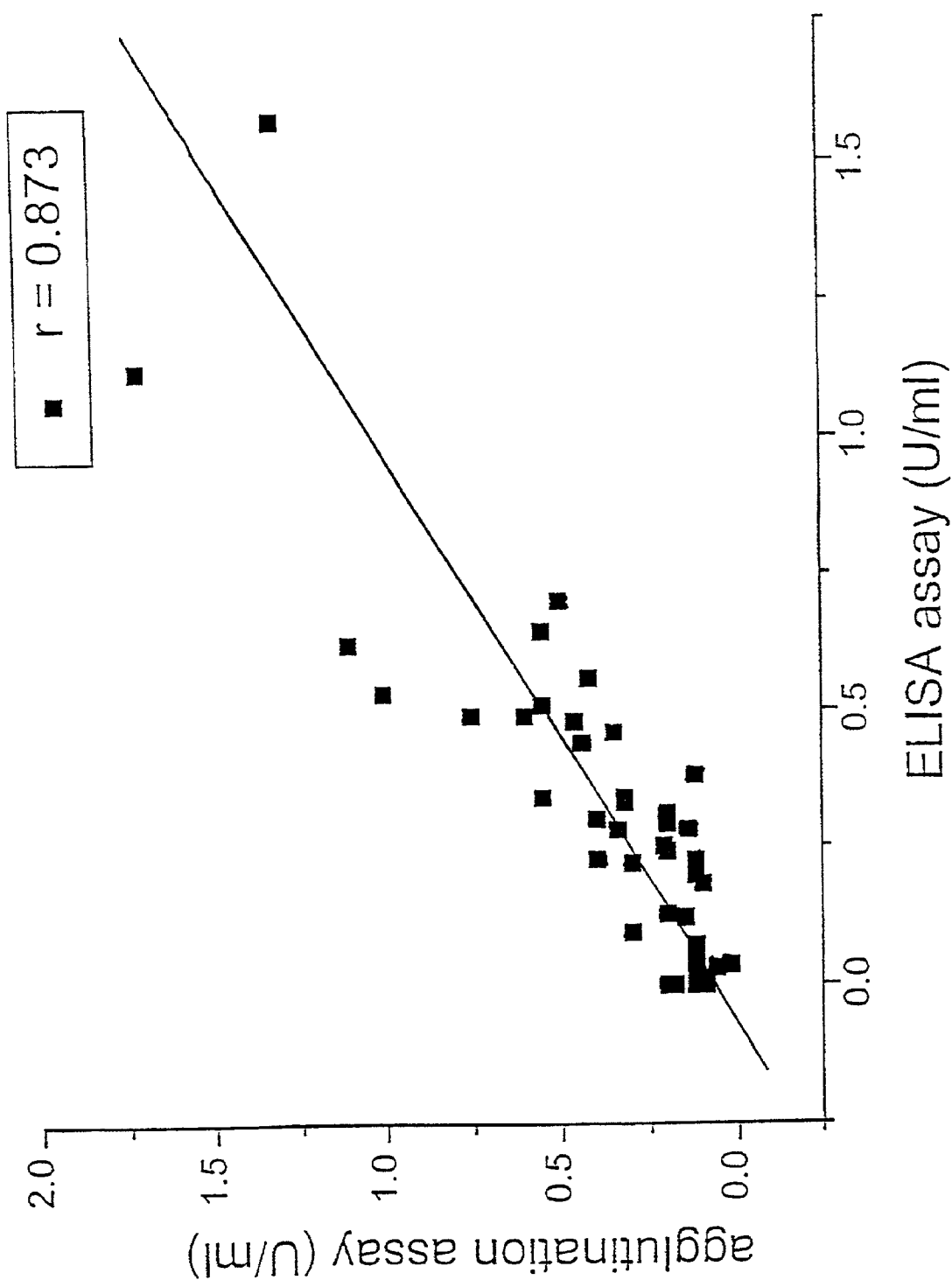

FIG. 6: Scatter plot analysis of vWF:RiCof determined in the ELISA assay and in the agglutination assay (n=44)

Values measured in the ELISA test were determined as described, values of the agglutination test were kindly provided by Dr. C. Mazurier and Dr. K. Peerlinck.

The invention is now to be illustrated by reference to the following examples which are merely illustrative and are not be construed as being a limitation of the scope of the present invention.

EXAMPLE 1

Preparation of Samples, Monoclonal Antibodies and Preparation and Purification of a Soluble Form of Glycoprotein Ib(α)

Blood was drawn from 22 healthy volunteers on 3.13% sodium citrate (9:1 vol/vol). Platelet-poor plasma was prepared by centrifugation at 2 000 rpm for 10 min. Plasma from vWD patients were a generous gift from Dr. C. Mazurier (Lille, France) and Dr. K. Peerlinck (KU.Leuven, Belgium).

The plasma pool was composed of the plasma of 25 normal individuals and was calibrated against a plasma pool of 50 healthy individuals (gift from Dr. C. Mazurier, Lille).

Frozen plasma was thawn, incubated for 5 min at 37° C., fractionated and stored at −80° C. Before use fractions were again incubated for 5 min at 37° C. Fractions were only used twice.

Monoclonal antibodies have been prepared according to standard protocols.

The anti-GPIbα monoclonal antibodies (mAb) used in this study were produced and characterized employing the following brief protocol. Murine anti-GPIb MoAbs were prepared according to the methods described by Köhler and Milstein, loc. cit. BALB/c mice were immunized by injection of purified GPIb. Two days after the last immunization, the spleen cells were fused with Sp2/0 mouse myeloma cells and cultured in HAT selection medium (GIBCO). Cloning was performed by the limiting dilution method using 96-well mictrotitre plates with mouse peritoneal macrophage feeder layers. This cloning resulted in a statistical probability of monoclonality greater than 99%. Hybridomas producing anti-GPIb antibodies were analyzed in ELISA using plates coated with purified GPIb and further screened in an agglutination assay in 96-well microplates as previously described (Depraetere, Blood 91 (1998), 3792-3799). Ascitic fluid rich in anti-GPIb antibodies was prepared by intraperitoneal injection of Pristane-pretreated BALB/c mice with $5 \times 10^6$ hybrid cells. IgG was purified from ascitic fluid by chromatography on protein-A-Sepharose CL-4B (Pharmacia). Antibody concentration was measured spectrophotometrically, using 1.35=1 OD unit. The immunoglobulin subtype was determined using an ELISA kit (Sigma). F(ab')$_2$ fragments were prepared from 27A10 by pepsin (Sigma) digestion using a pepsin/protein ratio 1/50 (wt/wt) and further purified on protein-A-Sepharose CL-4B. On SDS-polyacrylamide gel electrophoresis under nonreducing conditions, the 27A10 F(ab')$_2$ gave a single band with a molecular weight of ≅110,000 kD. Two well-characterized anti-GPIb MoAbs, AP-1 and 6D1 were kindly provided by Drs. T. J. Kunicki (Milwaukee, Wis.) and B. S. Coller (SUNY Stony Brook, N.Y.) respectively.

MAbs 12G1 and 6B4 are conformation-dependent anti-GPIbα mAbs that inhibit the ristocetin-induced human platelet agglutination. mAbs 2D4 and 7D2 are also conformation-dependent anti-GPIbα mAbs with no functional characteristics. MAb 1C1E7 is an anti-vWF-antibody that enhances the ristocetin induced binding of vWF to GPIb (Tornai, J Clin Invest 1993; 91:273-82).

MAb 701 is an anti-(vWF A1 domain)-antibody that inhibits the ristocetin and botrocetin induced platelet (Obert, Blood 1999; 93: 1959-1968). MAb 82D6A3 is an anti-(vWF A3 domain)-antibody that inhibits the binding of vWF to collagen type I and III (Hoylaerts, Biochem J 1997; 324:185-91).

The inhibitory mAb 12G1 was biotinylated using NHS LC Biotin (sulfosuccinimidyl 6-(biotinamido)hexanoate) from Pierce (Rockford, Ill.) according to the manufacturer's instructions.

Culture of CHO Cells Expressing rGPIbα Fragment (His1-Val 289)

The CHO cells expressing the soluble rGPIbα fragment (His1-Val289) were a generous gift from Dr. S. Meyer (Basel, Switzerland) (Schumpp-Vonach, Cytotechnology 1995; 17:133-41). CHO cells were cultured in a miniPERM bioreactor with a dialysis membrane of 12.5 kD (Heraeus Instruments GmbH, Hanau, Germany) (Falkenberg, Immunol Methods 1995; 179:13-29) according to the manufacturer's instructions.

Briefly, first cells were cultured in CHO-S-SFMII medium (GIBCO-BRL, Paisley, Scotland) supplemented with 1% ULTROSER®G (a serum substitute), 200 μg/ml STREPTOMYCIN, 200 U/mL penicillin (GIBCO-BRL) and 0.3% anti-FOAM a (Heraeus Instruments GmbH) in T culture flasks (180 mm 3). After reaching confluency, the cells were harvested by adding 1 mM EDTA. The cells ($5 \times 10^6$/ml) were then injected in the production module of the miniPERM bioreactor and were continuously cultured in this system over a period of two months. The culture medium in the nutrient module was replaced every second day. The medium containing the rGPIbα fragment (His1-Val289) was harvested twice a week, cells were removed by centrifugation and the following protease inhibitors were added to the supernatant: 20 μM leupeptin (Sigma, St. Louis, USA), 1 mM PMSF (Sigma) and 1 mM N-ethylmaleimide (ICN, Ohio, USA). The supernatant was stored at −80 C prior to purification.

Purification of the rGPIbα Fragment (His1-Val 289)

The recombinant protein was purified as described (Schumpp-Vonach, Cytotechnology 1995; 17: 133-41) with some modifications. For purification, immunoaffinity chromatography was used. The anti-GPIb-mAb 12G1 was coupled to CNBr-activated SEPHAROSE® 4B (affinity purification beads provided by Pharmacia Biotech, Uppsala, Sweden) according to the manufacturer's instructions. Before loading on the column, the pooled supernatant harvested from the miniPERM bioreactor was concentrated 5 times using a CH$_2$PR Concentrator S$_1$Y$_3$ (Amicon, USA). The column was washed with TBS, 0.3 mM CHAPS (Boehringer Mannheim) and bound proteins were eluted with 0.1 M glycine-HCl pH 2.8. The pH of the eluted fractions was neutralized immediately by the addition of 1M Tris-HCl pH 9. The fractions containing the rGPIbα fragment were identified in a sandwich ELISA (cr. infra). Peak fractions were pooled, the concentration of the rGPIbα fragment (His1-Val289) was determined using the Bradford kit (Biorad, Hercules, USA) with bovine serum albumin as a standard and the pooled fractions were stored at −80° C. until further use. Purity of the recombinant fragment in the pooled eluted fraction was evaluated by SDS-polyacrylamide gel electrophoresis.

EXAMPLE 2

ELISA-Tests

Sandwich ELISA

Microtiter plates (96 well, Greiner, Frickenhausen, Germany) were coated overnight at 4° C. with 100 μl/well mAb 2D4 (5 μg/ml in PBS). Plates were blocked with 3% milkpowder (250 μl/well) for 2 hours at RT, then 50 μl of each fraction from the column eluate was added to 50 μl TBS and samples were incubated for 1.5 hours at 37° C. The rGPIbα fragment (His1-Val289) present, was detected after 1 h incubation at 37° C. with biotinylated mAb 12G1 (100 μl/well), followed by a 45 min incubation with streptavidin-POD (Boehringer Mannheim) (100 μl/well) (1/10 000 in TBS, 0.1% Tween-20). Visualisation was performed with orthophenylenediamine (OPD, Sigma) and the colouring reaction was stopped with 4 mol/L H$_2$SO$_4$. The absorbance was determined at 490 nm. After each incubation step the plates were washed with TBS, 0.1% Tween-20, three times after coating and blocking steps and twelve times elsewhere.

VWF:CBA Assay

Microtiter plates (96 well) were coated overnight at 4° C. with human collagen type I (25 μg/ml, 100 μl/well) (Sigma). The human type I collagen used, was dialysed for 48 h against PBS. Plates were blocked with 3% milkpowder for 2 hours at RT (250 μl/well). Next, dilution series (1/2 in 0.3% milkpowder) of plasma pool and test samples were added starting from 1/80 to 1/640 (100 μl/well) and samples were incubated for 1.5 h at RT. Plasma pool was always added in triplicate and test samples in duplicate. Bound vWF was detected with anti-vWF-Ig-HRP (1/3 000 in 0.3% milkpowder) after 1 h incubation at RT. Visualisation was performed as described above. After each incubation step the plates were washed with PBS, 0.002% Tween-80 as described above.

Competition ELISAS

Competition Between vWF and Anti-GPIb-mAbs for Binding to the rGPIbα Fragment

The ELISA was performed as described for the vWF: RiCof ELISA except that serial dilutions of mAbs 6B4 and 7D2 (starting from 25 µg/ml, 50 µl/well) were preincubated for 30 min with rGPIbα fragment at 37° C. Than, 50 µl of a constant concentration of plasma pool (0.064 U/ml vWF) was added to each well. Samples were incubated for 1.5 hours at 37° C. before bound vWF was detected after incubation with anti-vWF-Ig-HRP.

Competition Between vWF and Anti-vWF-mAbs for Binding to the rGPIbα Fragment

The ELISA was performed as described for the vWF:RiCof ELISA except that serial dilutions of mAbs 701 and 82D6A3 (starting from 50 µg/ml, 100 µl/well) were preincubated for 30 min with 100 µl of a constant concentration of plasma pool (0.064 U/ml vWF) in a preblocked plate. Hundred µl of these solutions was than added to the rGPIbα fragment containing wells and samples were incubated for 1.5 hours at 37° C. before bound vWF was detected after incubation with anti-vWF-Ig-HRP.

Competition Between vWF and Anti-vWF-mAbs for Binding to Human Collagen Type I

The ELISA was performed as described for the vWF:CBA ELISA except that serial dilutions of mAbs 82D6A3 and 701 (starting from 0.2 µg/ml, 100 µl/well) were preincubated for 30 min with 100 µl of a constant concentration of plasma pool (100 ng/ml vWF) in a preblocked plate. Samples were than added to each collagen containing well and were incubated for 1.5 hours at 37° C. before bound vWF was detected after incubation with anti-vWF-Ig-HRP.

Ristocetin Induced Binding of vWF in the Presence of 1C1E7

Coating, blocking and incubation with rGPIbα fragment was as described for the vWF:RiCof ELISA. Then, before the plasma pool (pool of plasmas from normal, healthy donors plasmas) was added to each well, mAb 1C1E7 (25 µg/ml, 100 µl/well) was preincubated with constant amounts of plasma pool (100 µl/well, 0.064 U/ml vWF) for 30 min at RT. The samples were then added to the rGPIbα fragment-containing wells in the presence of different concentrations of ristocetin (0-600 µg/ml), and were incubated for 1.5 hours at 37° C. Bound vWF was detected as described before.

Bound vWF was detected with rabbit anti-human von Willebrand factor antiserum labeled with horse radish peroxidase (anti-vWF-Ig-HRP, Dako, Glostrup, Denmark) (1/3 000 in TBS, 0.1% Tween-20) after 1 h incubation at RT. Visualisation was performed with OPD and the colouring reaction was stopped with 4 mol/L $H_2SO_4$. The absorbance was determined at 490 nm. After each incubation step the plates were washed with TBS, 0.1% Tween-20, three times after coating and blocking steps and twelve times elsewhere.

VWF:AG Assay

Microtiter plates (96 well) were coated overnight at 4° C. with 125 µl/well of a polyclonal anti-vWF-Ig-solution (Dako) (1/1 000 in 50 mM carbonate buffer pH 9.6). The plates were blocked for 2 h at (RT) with 250 µl/well of a 3% milkpowder solution. Then, as a standard, a plasma pool (in triplicate) was applied to the wells at 1/40 to 1/2560 dilutions (samples were diluted in 0.3% milkpowder). The test (patient) samples were applied in duplicate in the same dilutions. All samples were incubated for 2 h at 37° C. Bound vWF was detected with anti-vWF-Ig-HRP (1/3 000 in 0.3% milkpowder) after 1 h incubation at RT. Visualisation was performed as described above. After each incubation step the plates were washed with TBS, 0.1% Tween-20 as described above.

VWF:RiCof-ELISA

Microtiter plates (96 well) were coated overnight at 4° C. with 100 µl/well mAb 2D4 (5 µg/ml in PBS). Plates were blocked with 3% milkpowder (250 µl/well) for 2 hours at RT followed by a 2 hour incubation at 37° C. with a solution containing 2.5 µg/ml rGPIbα fragment (His1-Val289) (in TBS, 0.1% Tween-20, 100 µl/well). Binding of vWF to the rGPIbα fragment (His1-Val289) was performed in the presence of ristocetin (Ristocetin A $SO_4$, abp, New York) for 1.5 h at 37° C. Therefore, plasma pool (healthy donors) and test samples (patient samples) were diluted 1/32 to 1/512 and 1/32 to 1/256 respectively in TBS, 0.1% Tween-20 containing 760 µg/ml ristocetin and 100 µl of each dilution was added to the rGpIbα coated wells. Plasma pool was always added in triplicate and test samples in duplicate.

Bound vWF was detected with rabbit anti-human von Willebrand factor antiserum labeled with horse radish peroxidase (anti-vWF-Ig-HRP, Dako, Glostrup, Denmark) (1/3 000 in TBS, 0.1% Tween-20) after 1 h incubation at RT. Visualisation was performed with OPD and the colouring reaction was stopped with 4 mol/L $H_2SO_4$. The absorbance was determined at 490 nm. After each incubation step the plates were washed with TBS, 0.1% Tween-20, three times after coating and blocking steps and twelve times elsewhere.

EXAMPLE 3

Ristocetin Induced Binding of Plasma vWF to the rGPIbα Fragment (His1-Val289)

The binding of plasma vWF to the captured rGPIbα fragment (His1-Val289) in the presence of varying concentrations of ristocetin was tested in an ELISA setup as described hereinabove. The binding curves were always studied starting from a 1/32 dilution of plasma as in more concentrated plasma less binding was observed probably due to non specific interference of ristocetin with the plasma proteins present. A good binding of vWF to rGPIbα fragment (His1-Val289) was observed in the presence of 760 µg/ml ristocetin (FIG. 1).

The specificity of the binding of vWF to rGPIbα fragment in the presence of ristocetin was assessed by studying this binding in the presence of anti-GPIb-mAbs 6B4 and 7D2 and in the presence of anti-vWF-mAbs 1C1E7, 701 and 82D6A3. Preincubation of rGPIbα fragment with mAbs 6B4 and 7D2 revealed 100 percent inhibition in the presence of mAb 6B4 (an anti-GPIbα-mAb that inhibits ristocetin induced platelet agglutination, N.C., submitted) while the non-inhibiting anti-GPIbα-mAb 7D2 had no effect (FIG. 2A). Preincubation of vWF with mAb 1C1E7 (an anti-vWF-mAb that enhances the ristocetin induced binding of vWF to GPIb, (17) showed an increase in vWF binding to the rGPIb□ fragment in the presence of even low concentrations of ristocetin (FIG. 2B). Preincubation of vWF with mAbs 701 and 82D6A3 showed a 100 percent inhibition in vWF binding to rGPIbα fragment in the presence of the anti-(vWF A1 domain) mAb 701 (which inhibits the ristocetin induced platelet agglutination, Girma, JP, personal communication) while the anti-(vWF A3 domain) mAb 82D6A3 (18) had no effect (FIG. 2C). Preincubation of mAb 82D6A3 with vWF however, resulted in 100 percent inhibition of the binding of vWF to collagen (FIG. 2D) while the anti-(vWF A1 domain) mAb 701 had no effect in collagen binding (FIG. 2D) as expected.

These data show that the ristocetin induced binding of vWF to GPIb, which is routinely tested in a platelet agglutination assay, can be reproducibly studied in an ELISA setup and that this test can be used to diagnose patients with vWD. It was demonstrated that vWF in plasma binds to a captured rGPIbα-fragment in the presence of ristocetin (FIG. 1). This binding was furthermore specific since (i) the vWF-GPIb interaction could be inhibited by mAb 6B4, that inhibits the ristocetin-induced platelet agglutination and (ii) since mAb 1C1E7, an anti-vWF-antibody that enhances the ristocetin induced binding of vWF to GPIb (Tornai, J Clin Invest 1993; 91:273-82) could also significantly increase this ristocetin induced binding (FIG. 2).

Inhibition of Ristocetin-Induced Binding of vWF to Purified GPIb by MoAbs Measured in an ELISA-Setup This assay was performed as previously described (Harsfali, Blood 1995; 85:705-11). Briefly, purified GPIb was coated onto wells of microtitre plates at 5 μg/mL, after blocking of non-adsorbed sites with BSA (10 mg/mL), the wells were preincubated with anti-GPIb MoAbs during 30 minutes at 22° C. Then vWF (10 μg/mL) and ristocetin (various concentrations) were added to the plate. The GPIb-associated vWF was revealed by a HRP-conjugated polyclonal anti-vWF antibody (Dako, Glostrup, Denmark) and ortho-phenylenediamine (OPD, Sigma). The reaction was stopped with 4 mol/L $H_2SO_4$ and absorbance determined at 492 nm. Non-specific vWF binding was measured by repeating the same ELISA on a non-coated microtitre plate.

Inhibition of Ristocetin or Botrocetin-Induced Binding of $^{125}$I-vWF to Washed Fixed Platelets by MoAbs Binding of $^{125}$I-vWF to washed fixed platelets was studied essentially as previously described (Sakariassen, J. Lab. Clin. Med. 102 (1983), 522). A final concentration of $10^8$ platelets/mL were premixed for 30 minutes with 10 μg/mL of the various anti-GPIb MoAbs. After adding $^{125}$I-vWF (0.5 μg/mL) binding was induced by the addition of ristocetin (various concentrations) or botrocetin (0.1 μg/mL, f.c.). Following 45 minutes of incubation, duplicate aliquots of the mixture were layered onto 20% sucrose cushions. The bound and free $^{125}$I-vWF was separated by centrifugation and counted. The percentage of total bound radioactivity was calculated as bound/(free+bound)radioactivity*100. Results are illustrated in the following table:

1998; 80:863) and in testing normal vWF (Fischer, Thromb Res 1998; 91:39-43) and its usefulness still has to be proven.

Some laboratories are using the collagen binding assay in vWD diagnosis. Although it is not a routine test, it has already been proven to be usefull in determining the vWF activities in many studies. It has been proposed by some authors to replace the vWF:RiCof measurements (Brown, Thromb Res 1986; 43:303-11, Favaloro, Pathology 1993; 25:152-8), but it has to be noticed that both tests are based on different binding characteristics of vWF. VWF binds to collagen mainly through its A3 domain (Lankhof, Thromb Haemost 1996; 75:950-8) whereas vWF binding to GPIb occurs through the A1 domain (Sixma, Eur J Biochem 1991; 196:369-75). This is shown in FIGS. 2C and D where the anti-(A1 vWF domain) mAb 701 inhibits the ristocetin induced binding of vWF to rGPIbα fragment, whereas the anti-(A3 VWF domain) mAb 82D6A3 has no effect. The latter mAb however inhibits the binding of vWF to collagen in contrast to 701.

EXAMPLE 4

The Use of the vWF:RiCof-ELISA as a Reliable Test to Determine Unknown vWF:RiCof Activities The vWF:RiCof activity of a dilution series of plasma pool (1/32 to 1/512) was measured in the ELISA setup. Plotting the OD (490 nm) versus the vWF:RiCof activity resulted in a binding curve of plasma vWF to rGPIbα which could best be fitted by the use of polynomial regression ($y=A_0+A_1x+A_2x^2$, FIG. 3). The vWF:RiCof activity in test samples can then be calculated as follows:

$$x=(-A_1+((A_1)^2-4A_2(A_0-y))^{1/2})/2A_2$$

with x=unknown vWF:RiCof activity (U/ml)
y=measured OD (490 nm)
$A_0, A_1, A_2$, constants in equation $y=A_0+A_1x+A_2x^2$

| MoAb | Subtype | Ristocetin (1.2 mg/mL) induced human platelet aggregation | Botrocetin (0.5 μg/mL) induced human platelet aggregation | Shear-induced human platelet adhesion to collagen type I (shear rate 2600/s) in Sakariassen type flow chamber Data given is % surface coverage in comparison to control (= platelet adhesion in the absence of Ab is thus set as 100%) |
| --- | --- | --- | --- | --- |
| 2D4 | IgG1 | No inhibition | No inhibition | ND |
| 6B4 | IgG1 | 1 μg/mL Ab results in full inhibition | 1 mg/mL Ab results in full inhibition | Tests done with 5 μg/mL Ab: 4.2% ± 1.4 (SEM) |

ND non determined
SEM standard error of mean with n = 3

Recently another ELISA assay was developed as an alternative for the vWF:RiCof agglutination assay (Murdock, Thromb Haemost 1997; 78:1272-7). In this test, a mAb that recognises an epitope on vWF-A1 domain important in its interaction with GPIb, was used. This assay however has been shown to give widely differing results from the vWF:RiCof assay in an UK NEQAS Survey (Preston, Thromb Haemost The repeatability of this test was determined by assaying 5 dilutions of plasma pool (1/32, 1/64, 1/128, 1/256, 1/512) on six replicates in one run. The coefficient of variation (CV) was always less than 13% (4%, 8%, 10%, 12%, 11% respectively). The reproducibility was determined by testing the same control samples on six replicates over 3 days and this by two technicians. The maximum CV observed for each data point was 13%, 9%, 13%, 9% and 10% respectively.

Polynomial regression line calculation showed an intra-assay correlation of 0.9984±0.0018 and an inter-assay correlation of 0.9978±0.00189.

To determine the detection limit and quantification limit of the vWF:RiCof-ELISA, six replicates of nine dilutions (1132 to 118 192) of plasma pool were tested in three assays. The detection limit (DL) in the vWF:RiCof-ELISA (defined as 3SD above the mean of zero standard) was 0.0005 U/ml (112 048 plasma dilution). The quantification limit (QL), i.e. the minimum concentration that can be measured from assay to assay with CV<20% was 0.0005 U/ml (1/2 048 plasma dilution).

EXAMPLE 5

VWF:RiCof in Plasma from Normal Individuals Compared to vWF:CBA and vWF:Ag

The vWF:RiCof activity was determined in the plasma from apparently normal adult volunteers (n=24) using the ELISA based system. The vWF:RiCof activity in the plasma of all these normal individuals ranged from 0.46 U/ml to 1.6 U/ml (median 0.75 U/ml) (FIG. 4). Determination of vWF:CBA and vWF:Ag in these plasmas revealed activities that correlated well with the vWF:RiCof activity (FIG. 4). Plotting vWF:RiCof versus vWF Ag revealed a correlation of 0.82, vWF:RiCof versus vWF:CBA led to a correlation of 0.80, as expected for normal individuals.

EXAMPLE 6

Measurement of vWF Activities in Plasmas of vWD Patients

Plasma samples of 45 vWD patients of known subtype were analysed for vWF:RiCof with the ELISA based assay (FIG. 5). For type 1 vWD patients (n=17), the values ranged from 0.005 U/ml to 0.559 U/ml (median, 0.28 U/ml). In the plasma of the type 2A (n=18) and the 4 type 2B vWD patients examined, vWF:RiCof values of 0.005 U/ml to 0.38 U/ml (median 0.055 U/ml) were measured and of 0.005 U/ml to 0.34 U/ml (median 0.094 U/ml) respectively. The vWF:RiCof activities in the plasmas of the 3 type 3 vWD patients available were below 0.0005 U/ml (QL in the ELISA assay). The vWF in plasma of 2 type 2N patients had normal vWF:RiCof activiies (0.87 U/ml and 0.62 U/ml). The vWF:RiCof activity determined in the ELISA test was compared to the vWF:RiCof activity determined in the agglutination test. The latter data were kindly provided by Dr. C. Mazurier and Dr. K. Peerlinck. A correlation of 0.828 was obtained (FIG. 6).

In type 1 patients, the vWF:RiCof, vWF:CBA (median, 0.34 U/ml) and vWF:Ag (median, 0.34) activities are proportional, as there is no functional defect in vWF (FIG. 5). This resulted in vWF:Ag/vWF:RiCof and vWF:Ag/vWF:CBA ratios around one (median: 1.23 U/ml and 0.964 U/ml respectively). In type 2A and 2B patients, the functional defect was clear as vWF:RiCof and vWF:CBA (median 0.146 U/ml and 0.31 U/ml respectively) were low. vWF:Ag was low or normal (median: 0.16 U/ml and 0.31 U/ml respectively) in these patients (FIG. 5). In the type 3 patients there was a clear quantitative defect as almost no vWF:Ag activity was measured. The 2 type 2N patients showed normal vWF:Ag and vWF:CBA activities in accordance with the vWF:RiCof activity.

It was shown that this vWF:RiCof-ELISA can be used to discriminate (i) between normal individuals and vWD patients and (ii) between type 2A and type 2B patients. (i) The vWF:RiCof activity of plasma vWF of all normal individuals was >50% (except for one patient). These results corresponded with the vWF:CBA and the vWF:Ag values, resulting in vWF:Ag/vWF:RiCof and vWF:Ag/vWF:CBA ratios around one (median: 1.23 U/ml and 0.96 U/ml respectively). On the other hand, the type 1 vWD patients had vWF:RiCof <50% (except for one patient) and had comparable vWF:CBA and vWF:Ag activities since this indeed is a quantitative and not a qualitative disorder (FIG. 5). The type 2A and 2B patients had low vWF:RiCof compared to low or normal vWF:Ag. In the 3 available type 3 patients no detectable vWF:RiCof, vWF:CBA or vWF:Ag activities were observed. The 2 type 2N patients had no abnormalities in any of the vWF activities measured. In conclusion, vWF:RiCof values determined in the ELISA setup correlated well with the values obtained from platelet agglutination studies (see FIG. 6).

The invention claimed is:

1. A method for discriminating between types of von-Willebrand disease using a von-Willebrand factor (vWF) binding activity, the method comprising the steps of:
   (a) detecting the binding activity of vWF in a sample to a soluble form or a portion of glycoprotein 1b(α) (GP1b (α)) that is not associated with a platelet in the presence of ristocetin or a functionally equivalent substance, wherein the soluble form or portion of GP1b(a) is presented by an anti-GP1b(α) antibody;
   (b) determining an amount of vWF-antigen in said sample;
   (c) determining a ratio between the binding activity detected under step (a) and the amount of vWF-antigen determined under step (b) for said sample;
   (d) comparing the ratio obtained under (c) to a reference range; and
   (e) discriminating between types of von-Willebrand disease based using the comparison result obtained under step (d).

2. The method of claim 1, wherein detecting the binding activity under step (a) comprises detecting formation of a complex comprising vWF and the soluble form or the portion of GP1b(α).

3. The method of claim 1, wherein said anti-GP1b(α) antibody is bound to a solid support.

4. The method of claim 2, wherein said complex is bound to a solid support by the anti-GP1b(α) antibody.

5. The method of claim 1, wherein detecting the binding activity under step (a) comprises using an anti-vWF antibody.

6. The method of claim 1, wherein detecting the binding activity under step (a) comprises using a heterogeneous or homogeneous assay.

7. The method of claim 6, wherein detecting the binding activity under step (a) comprises using an heterogeneous assay selected from the group consisting of enzyme linked immunosorbent assay (ELISA), a radioimmunoassay (RIA), an immunoradiometric assay (IRMA), a fluorescent immunoassay (FIA), a chemiluminescent immunoassay (CLIA) and an electrochemiluminescent immunoassay (ECL).

8. The method of claim 6, wherein detecting the binding activity under step (a) comprises using an homogeneous agglutination assay.

9. The method of claim 1, wherein the sample is obtained from blood, serum or plasma of a patient.

10. The method of claim 1, wherein the soluble form or the portion of GP1b(α) is a recombinant protein.

11. The method of claim 1, wherein said anti-GP1b(α) antibody is a monoclonal antibody, a polyclonal antibody, a synthetic antibody, or a fragment of an antibody.

12. The method of claim 1, wherein said anti-GP1b(α) antibody is detectably labeled.

13. The method of claim 3, wherein said solid support is selected from a group consisting of plastic, glass, silicon, metal, polystyrene, polyvinyl chloride, polypropylene, polyethylene, polycarbonate, dextran, nylon, amylose, natural or modified cellulose, polyacrylamide, agarose, magnetide and any combinations thereof.

14. The method of claim 13, wherein said solid support comprises a latex bead.

15. The method of claim 8, wherein said agglutination is measured by electric field variation, magnetic field variation, turbidimetric variation or light scattering.

16. The method of claim 9, wherein the sample is diluted.

17. The method of claim 1, wherein the soluble form or the portion of GP1b($\alpha$) comprises an N-terminal domain of GP1b($\alpha$).

18. The method of claim 1, wherein the soluble form or the portion of GP1b($\alpha$) comprises amino acid residues His1-Val289 of GP1b($\alpha$).

19. The method of claim 1, wherein the detecting step (a) permits detecting the binding activity of vWF to the soluble form or the portion of GP1b($\alpha$) to a lower limit of 0.0005 U/mL of vWF with a coefficient of variation less than 20%.

20. The method of claim 1, wherein the sample is plasma or serum.

21. The method of claim 1, wherein discriminating between types of von-Willebrand disease (vWD) in step (e) comprises discriminating Type 1 vWD from Type 2 vWD.

* * * * *

UNITED STATES PATENT AND TRADEMARK OFFICE
CERTIFICATE OF CORRECTION

| | | |
|---|---|---|
| PATENT NO. | : 7,622,259 B1 | Page 1 of 1 |
| APPLICATION NO. | : 10/019740 | |
| DATED | : November 24, 2009 | |
| INVENTOR(S) | : Cauwenberghs et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 932 days.

Signed and Sealed this

Twenty-sixth Day of October, 2010

David J. Kappos
*Director of the United States Patent and Trademark Office*